United States Patent [19]
Hoye

[11] Patent Number: 5,543,523
[45] Date of Patent: Aug. 6, 1996

[54] METHOD AND INTERMEDIATES FOR THE SYNTHESIS OF KORUPENSAMINES

[75] Inventor: Thomas R. Hoye, St. Paul, Minn.

[73] Assignee: Regents of the University of Minnesota, Minneapolis, Minn.

[21] Appl. No.: 339,958

[22] Filed: Nov. 15, 1994

[51] Int. Cl.$^6$ .................................................. C07D 217/02
[52] U.S. Cl. ........................... 546/14; 546/146; 546/149; 546/150
[58] Field of Search ............................ 546/14, 146, 149, 546/150

[56] References Cited

FOREIGN PATENT DOCUMENTS

WO92/18125  10/1992  WIPO ...................................... 546/50

OTHER PUBLICATIONS

Rizzacasa et al, Aust. J. Chem, vol. 43, 1990, pp. 79–86.
Michael R. Boyd et al., "Anti–HIV Michellamines from *Ancistrocladus korupensis*," *J. Med. Chem.*, 37, 1740–1745 (1994).
Gerhard Bringmann et al., "The Synthesis of all Possible Isomeric 6,8–Dioxygenated 1,3–Dimethyl–1,2,3,4–tetrahydroisoquinoline Methyl Esters—Useful Chiral Building Blocks for Naphthylisoquinoline Alkaloids," *Liebigs Ann. Chem.*, 877–888 (1993).
Gerhard Bringmann et al., "The Absolute Configuration of Michellamine B, a 'Dimeric', Anti–HIV–Active Naphthylisoquinoline Alkaloid," *Angnew. Chem. Int. Ed. Eng.*, 32 1190 (1993).
Gerhard Bringmann et al., "'Biomimetic' Oxidative Dimerization of Korupensamine A: Completion of the First Total Synthesis of Michellamines A, B, and C," *Tetrahedron*, 50(32), 9643–9648 (1994).
Y. F. Hallock et al., "Korupensamines A–D, Novel Antimalarial Alkaloids from *Ancistrocladus korupensis*," *J. Org. Chem.*, 59, 6349–6355 (1994).
T. R. Kelly et al., "Convergent Total Synthesis of the Michellamines," *Tetrahedron Letters*, 35(41), 7621–7624, 10 Oct. (1994).
K. P. Manfredi et al., "Novel Alkaloids from the Tropical Plant *Ancistrocladus abbreviatus* Inhibit Cell Killing by HIV–1 and HIV–2," *J. Med. Chem.*, 34, 3402–3405 (1991).

*Primary Examiner*—C. Warren Ivy
*Assistant Examiner*—Zinna N. Davis
*Attorney, Agent, or Firm*—Schwegman, Lundberg, Woessner & Kluth, P.A.

[57] ABSTRACT

Activated isoquinolines and naphthalenes are disclosed which are useful to prepare korupensamines, michellamines and analogs thereof.

20 Claims, 1 Drawing Sheet

METHOD AND INTERMEDIATES FOR THE SYNTHESIS OF KORUPENSAMINES

This invention was made with the assistance of the National Institutes of Health under Grant Nos. RO1-GM34492 and CA-60 284. The U.S. Government has certain rights in the invention.

BACKGROUND OF THE INVENTION

Michellamines A (1), B (2), and C (3) constitute a family of anti-HIV, atropisomeric, naphthylisoquinoline alkaloids. All are fully protective against both HIV-1 and HIV-2 infected CEM-SS cells with $EC_{50}$ values of 2–13 µM. Michellamine B, the most studied and most prevalent of the group, completely protects MT-2 cells from both AZT-resistant and pyridone-resistant strains of HIV-1. The structure of michellamine B is shown below:

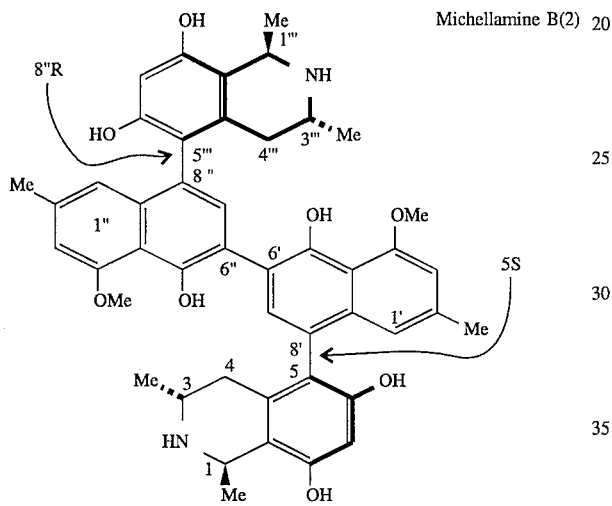

Michellamine B possesses a multilevel mode of action including an inhibition of the viral reverse transcriptase as well as blockage of cellular fusion and synctium formation. In light of these promising properties, as well as favorable initial toxicity evaluation, michellamine B has been selected by the National Cancer Institute for INDA-directed preclinical development. See, for example, K. P. Manfredi et al., *J. Med. Chem.*, 34, 3402 (1991) and M. R. Boyd et al., *J. Med. Chem.*, 37, 1740 (1994).

The michellamines were isolated from a previously unidentified plant, *Ancistrocladus korupensis*—a liana found only in the rain forest of a limited region in Cameroon. Supply continuity and sufficiency are important concerns for further drug development. Atropisomers 1–3 are unique among known naphthylisoquinoline alkaloids in their dimeric nature, in the locus of the naphthalene to isoquinoline biaryl bond, and in the extent of free hydroxyl group adornment. The relative configurations of the stereogenic biaryl axes in each of 1–3 were established by identification of NOE interactions between the peri-H(1') and -H(1''') and one or the other of the diastereotopic protons at C(4) and C(4'''). The absolute configurations at C(1)/C(1''') and C(3)/C(3''') were assigned by degradation to R-alanine and R-3-aminobutyric acid, respectively. See, M. R. Boyd et al., as cited above, G. Bringmann et al., *Angew. Chem. Int. Ed. Eng.*, 32, 1190 (1993) and G. Bringmann et al., *Tetrahedron*, 32, 9643 (1994). The configurations at 5/8' and 8''/5''' of michellamines A, B and C are S/S, S/R and R/R, respectively.

Two syntheses of michellamine A were recently described by G. Bringmann et al., *Tetrahedron*, 32, 9643 (1994), and T. R. Kelly et al., *Tetrahedron Lett.*, 35, 7621 (1994). An acyl derivative of a sample of the natural product korupensamine A (4), which co-exists with the michellamines in the plant, was oxidatively dimerized with silver oxide to yield a binaphthylidendione, which was reduced and deacylated to yield michellamine A. The structure of korupensamine A (4) and its atropisomer ("korupensamine C" (4')) are shown below:

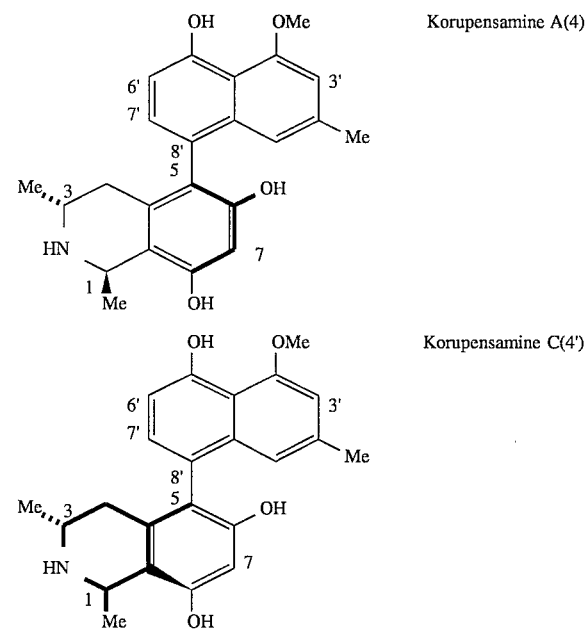

Compound 4' has been referred to as korupensamine B by G. Bringmann et al., *J. Org. Chem.*, 59, 6349 (1994). In view of the ability to synthesize michellamines from these compounds in no more than five steps, a need exists for synthetic methods and intermediates which can be employed to prepare korupensamines.

SUMMARY OF THE INVENTION

The present invention provides intermediates useful for the synthesis of korupensamines and thus for the synthesis of michellamines and their analogs. For example, the present invention provides a compound of the general formula (I):

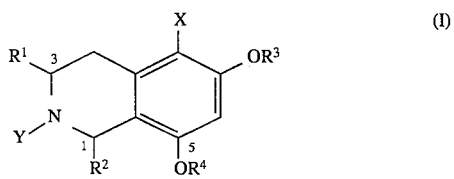

wherein X is Br, Cl or I; Y is H, $(C_1-C_4)$alkyl, benzyl, or CHO; each of $R^1$ and $R^2$ is H or $CH_3$ and each of $R^3$ and $R^4$ is H, $(C_1-C_4)$alkyl, benzyl, $(C_2-C_5)$acyl, or an acid labile hydroxy protecting group such as $(C_1-C_4)$alkoxy$(C_1-C_4)$alkyl, tetrahydropyranyl, or $(R^8)_3$Si, wherein each $R^8$ is $(C_1-C_4)$alkyl. Preferably, X is I, $R^1$ and $R^2$ are $CH_3$, and $R^3$, $R^4$ and Y are the same protecting group, i.e., $R^3=R^4=Y=$benzyl.

As shown in compound 2, a broken line indicates a bond that extends below the plane of the ring, i.e., below the plane of the page, and a wedged line indicates a bond that extends above the plane of the page. Thus, to prepare korupensamines A and C, the 1R,3R-isomer of (I) is employed. However, the procedures disclosed by G. Bringmann et al., cited above, permit the preparation of all the 1,3-isomers of formula (I), wherein X=H; hence all the 1,3-isomers of formula (I) are considered to be within the scope of the invention.

The present invention also provides compounds of the formula (II):

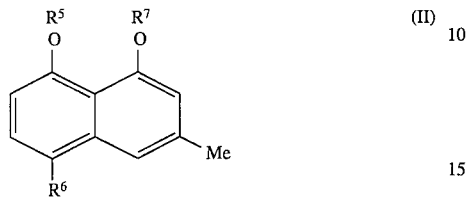

wherein $R^6$ is Cl, Br, I, B(OH)$_2$, an anhydride or ester of B(OH)$_2$, or OSO$_2$R$^9$, wherein R$^9$ is (C$_1$–C$_4$)perfluoroalkyl, and each of R$^5$ and R$^7$ is H, (C$_1$–C$_4$)alkyl, benzyl, (C$_2$–C$_5$)acyl or an acid-labile hydroxy protecting group, as described above. Preferably, $R^6$ is Br or B(OH)$_2$, $R^5$ is an acid-labile protecting group, and $R^7$ is H or CH$_3$.

The compound of formula II wherein $R^6$ is B(OH)$_2$ can be prepared from a compound of formula II wherein $R^6$ is halo, by lithiation and reaction of the lithiated compound with B(OMe)$_3$, following protection of the two OH groups, i.e., wherein $R^5$ and R$_7$ are not H or acyl. The compound of formula II wherein $R^6$ is B(OH)$_2$ and $R^5$ and $R^7$ are not H or acyl can be coupled via Pd(0) catalyzed coupling with a compound of formula I, wherein X is I, $R^1$=$R^2$=CH$_3$, and $R^3$, $R^4$ and Y are not H, to yield N- and 6,8,4', 5' hydroxyl-protected korupensamines. Selective removal of the 5' hydroxyl protecting group, followed by oxidative 6'/6' coupling, reduction and, if necessary, removal of the remaining $R^3$, $R^4$ and Y protecting groups, wherein $R^7$ is CH$_3$, affords a mixture of michellamines A–C, which can be separated by chromatographic techniques.

Thus, a further aspect of the present invention is a method to prepare a korupensamine, preferably korupensamine A or B, or an analog thereof comprising:

(a) reacting a compound of the formula (III):

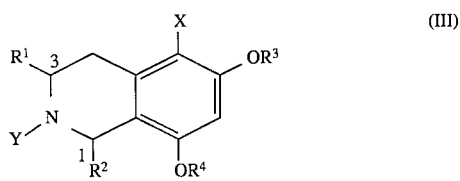

wherein each of $R^1$ and $R^2$ is CH$_3$ or H, X is I, Y is (C$_1$–C$_4$)alkyl, benzyl or CHO, and each of $R^3$ and $R^4$ is (C$_1$–C$_4$)alkyl, benzyl, (C$_2$–C$_5$)acyl or an acid-labile hydroxy protecting group; with a compound of the formula (IV):

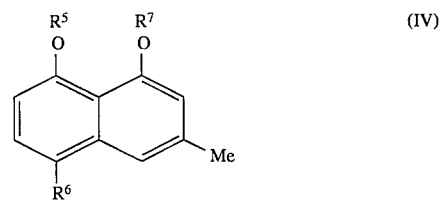

wherein $R^5$ is benzyl, (C$_2$–C$_5$)acyl or an acid-labile hydroxy protecting group, $R^6$ is B(OH)$_2$, and $R^7$ is (C$_1$–C$_4$)alkyl; in the presence of a Pd(0) catalyst and an inorganic base in an organic solvent, to yield a compound of the formula (V):

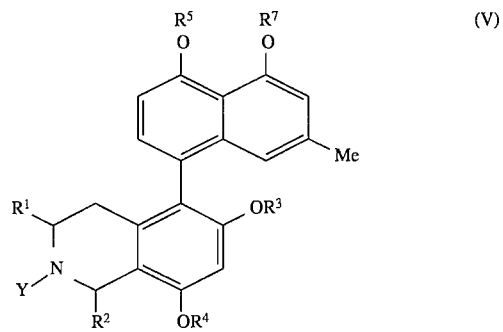

wherein Y, $R^1$, $R^2$, $R^3$, $R^4$, $R^5$ and $R^7$ are as defined above; and (b) removing protecting groups $R^3$, $R^4$, $R^5$ and Y to yield a compound of formula V wherein $R^1$ and $R^2$ are each H or CH$_3$, $R^7$ is (C$_1$–C$_4$)alkyl, and Y, $R^2$, $R^3$, $R^4$, and $R^5$ are H. Preferably, $R^1$, $R^2$ and $R^7$ are CH$_3$, $R^5$ is an acid-labile protecting group, preferably methoxymethyl, that is subsequently removed by exposing V to dilute aqueous acid, and Y, $R^3$ and $R^4$ are benzyl that are subsequently removed by hydrogenolysis. Most preferably, the 1R,3R-isomer of III is employed, which yields a mixture of korupensamines A and C.

DETAILED DESCRIPTION OF THE INVENTION

Figure 1:
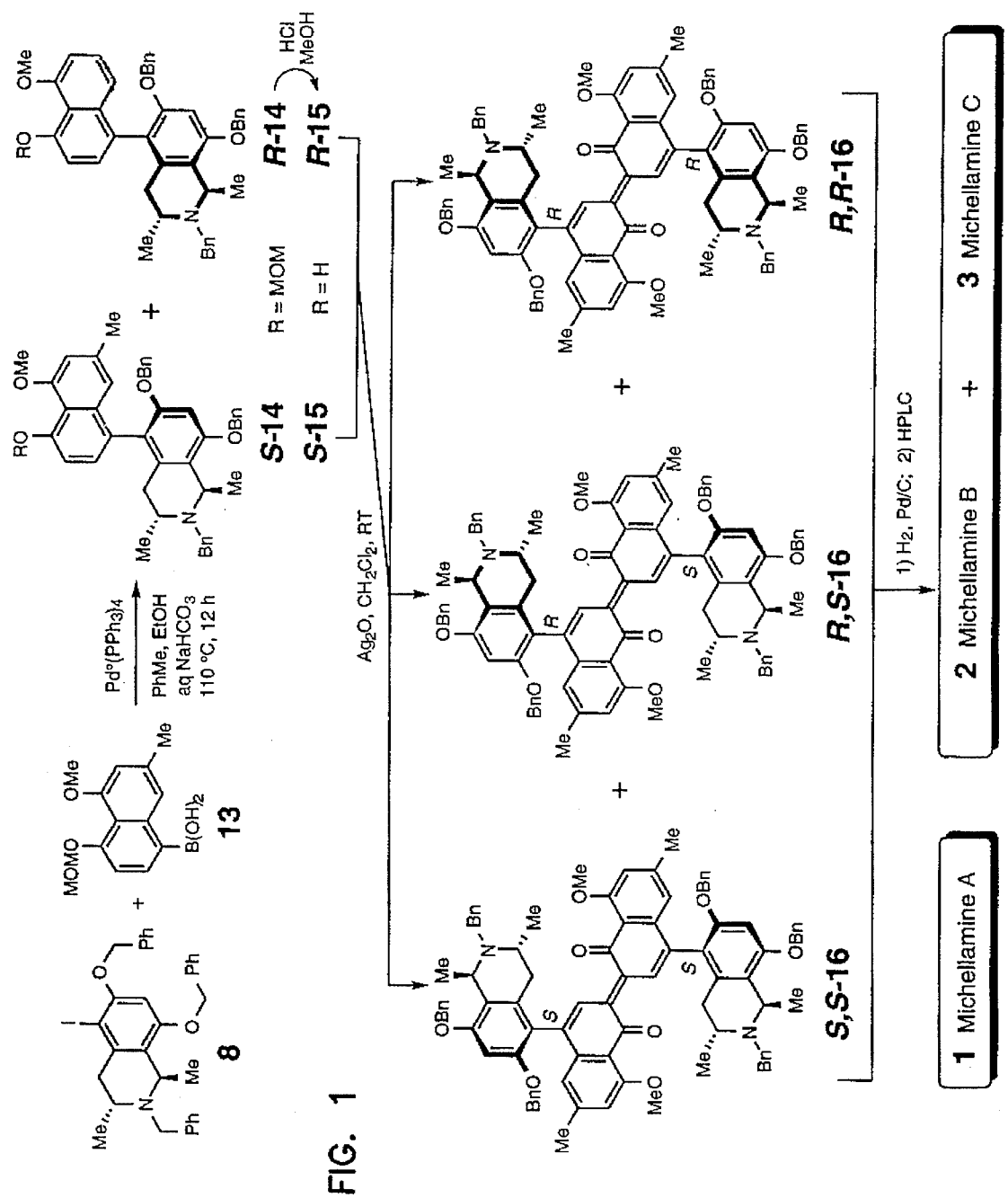
FIG. 1 is a reaction scheme summarizing the reaction of compounds 8 and 13 to yield korupensamine derivatives S-14 and R-14, and the conversion of these compounds to michellamines A–C.

As shown in Scheme I, following the general route developed by G. Bringmann et al., Angew. Chem. Int. Ed. End, 25, 913 (1986) and G. Bringmann, et al., Liebigs Ann. Chem., 877 (1993), the non-racemic tetrahydroisoquinoline 7 (I, Y=H, $R^1$=$R^2$=$R^3$=$R^4$=CH$_3$), was prepared from methyl 3,5-dimethoxybenzoate (5) via Raney nickel reduction of the non-racemic α-methylbenzylimine 6, following the methodology of D. E. Nichols et al., J. Med. Chem., 16, 480 (1973). Demethylation of 7 with excess boron tribromide gave a diphenol amine•HBr salt, which was tribenzylated with benzyl bromide and cesium carbonate in DMF at room temperature (85%, two steps). Regiospecific iodination with iodine and silver sulfate gave C(5)-activated, benzyl protected 8 (66%), in accord with the methodology of W. W. Wy, Tetrahedron Lett., 34, 6223 (1993). Likewise, direct bromination with Br$_2$ yields the corresponding brominated compound.

Scheme I.

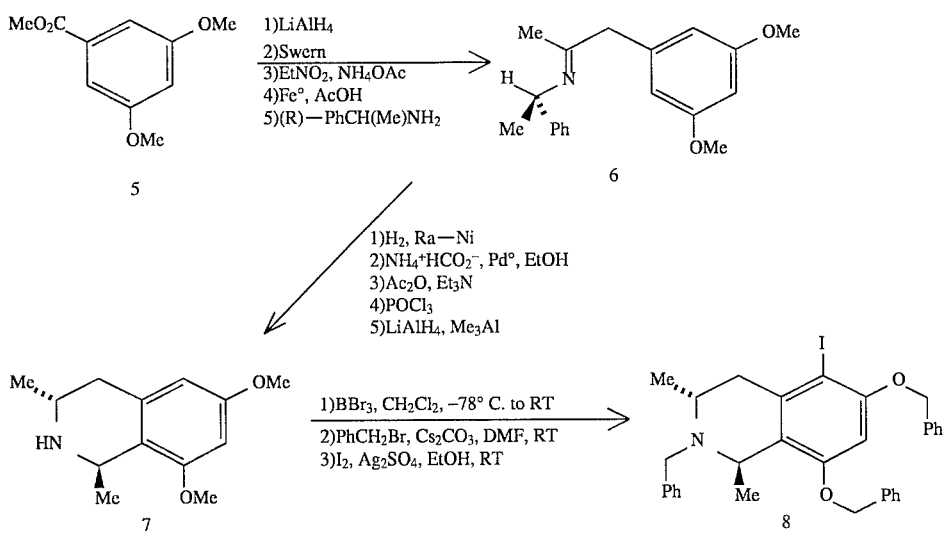

Generally, demethylation of 7 yields a compound of formula I wherein Y, $R^3$ and $R^4$ are H, and the hydroxyl groups can be reacted with other protecting groups, such as those disclosed hereinabove. Likewise, the iodo moiety can be replaced by Br or Cl by a variety of halogen exchange reactions, such as by lithiation, following reaction with elemental halogen. Replacement of (R)-PhCH (Me)$NH_2$ with $PhCH_2NH_2$ and/or reaction with the corresponding 3,5-dimethoxyphenylacetaldehyde yields compounds of formula I wherein $R^1$ and/or $R^2$ is H. Synthesis of all the possible 1,3-isomers of 7, as well as compounds of formula 7 wherein one OMe group has been replaced by OH, is disclosed by G. Bringmann, et al., Liebigs Ann. Chem., 877 (1993).

As shown in Scheme II, boronic acid 13 (II, $R^5=CH_2OCH_3$, $R^7=CH_3$, $R^6=B(OH)_2$ was efficiently prepared from methoxymethyl (MOM)-protected 2,4-dibromophenol (9) by a regiospecific benzyne annulation reaction. Treatment of 9 with an excess of lithium cyclohexylisopropylamide and N,N-diethyl seneciamide, as disclosed by M. Watanabe et al., Chem. Pharm. Bull., 34, 2810 (1986), gave 12 (II, $R^5=CH_2OCH_3$, $R^7=CH_3$, $R^6=Br$) presumably by way of benzyne 10 and lithium enolate 11. Although the yield of this reaction was only 29%, the transformation was very reproducible. O-Methylation with methylsulfate, lithiation, and boronic acid synthesis with $B(OCH_3)_3$ followed standard protocols to yield 13.

Reaction of a protected compound of formula II wherein $R^6=Li$ with $Cl_2$ or $I_2$ yields II, $R^6=Cl$ or I. Likewise, other acid-labile protecting groups can be used in place of $MeOCH_2$ in compound 9, and $R^7=CH_3$ in formula II can readily be replaced with other protecting groups.

Scheme II.

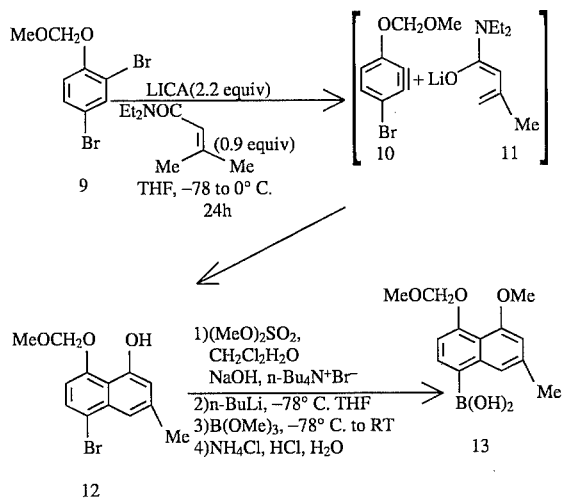

As shown in FIG. 1, the palladium(0) catalyzed cross-coupling of 8 with 13 provided an about 4:3 ratio of the hindered atropisomers S-14 and R-14 (40–80%). Palladium(0) catalyzed cross-coupling is typically carried out in the presence of a base and an organic solvent. A preferred embodiment of the invention utilizes tetrakis(triphenylphosphine)palladium(0) $(Pd(PPh_3)_4)$ as the source of palladium(0) catalyst, saturated sodium bicarbonate $(NaHCO_3)$ as the base and toluene as the organic solvent. Other useful sources of Pd(0) catalysts include those disclosed in Larock et al. (U.S. Pat. No. 5,233,059, Col. 6) and Blaser et al. (U.S. Pat. No. 4,335,054, Col. 6 and Col. 7), which may alternatively be used in the method of present invention under conditions wherein Pd(0) is generated. Bases useful in the present invention are those which are adequately soluble in the reaction medium. Although an inorganic base is preferred, an organic base can also be used. Representative bases are disclosed at Col. 7 of the Larock et al. patent, and Col. 7 of the Blaser et al. patent, as cited above. Examples of suitable organic solvents include, in addition to the preferred toluene, tetrahydrofuran, ethers, glycol ethers, dimethylsulfoxide, dimethyl formamide, acetonitrile, acetamide, dimethylacetamide, and hexamethylphosphoramide.

Hydrolysis of the methoxymethyl (MOM) ethers of 14 gave the naphthols 15 (75–100%), which could be separated by careful normal-phase HPLC. Hydrogenolysis of the benzyl groups in a mixture of the naphthols 15 provided an about 4:3 mixture of korupensamine A and "C" atropisomers 4 and 4'.

The mixture of tribenzylated naphthols 15 underwent remarkably efficient oxidative coupling with excess silver oxide in methylene chloride (or $CDCl_3$) at room temperature by the methodology of H. Laatsch, *Liebigs Ann. Chem.*, 1321, (1980), to give the purple indigoids R,S-16, S,S-16, and R,R-16 in an about 2:1:1 ratio (about 100%). The cross-ring quinones 16 could be reduced to the corresponding colorless binaphthols (sodium dithionite, $H_2O$, $CH_2Cl_2$ or $NaBH_4$, $CH_2Cl_2$, EtOH) and then perdebenzylated. More conveniently, direct exposure of 16 to one atmosphere of hydrogen in methylene chloride/methanol over 10% Pd/C resulted in simultaneous reductive bleaching of the indigoid and complete hydrogenolysis of the six benzyl groups. Michellamines A–C were cleanly (as judged from the crude $^1H$ NMR spectrum) produced with nearly quantitative mass recovery. Separation of a small portion on amino-bonded phase [7:1$CH_2Cl_2$:0.1 weight % $(NH_4)_2CO_3$ in methanol] has thus far provided a pure sample of michellamine A (1) along with an about 2:1 mixture of michellamines B (2) and C (3), as determined by NMR analysis.

The invention will further be described by reference to the following detailed examples.

EXAMPLE 1

Preparation of 1(R), 3(R)-1,2,3,4-tetrahydro-6,8-dihydroxy-1,3-dimethylisoquinoline hydrobromide salt (101)

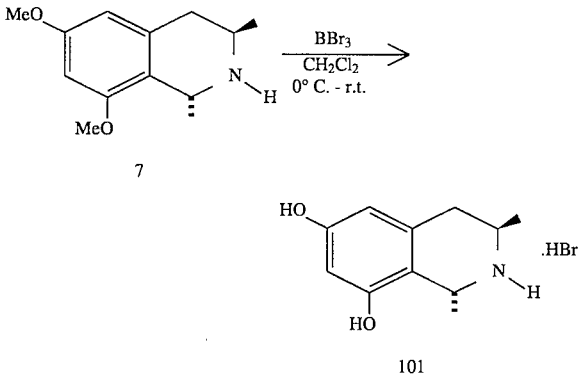

(1R, 3R)-1,2,3,4-tetrahydro-6,8-dimethoxy-1,3-dimethyl-isoquinoline was prepared as described in G. Bringmann et al., *Liebigs Ann. Chem.*, 877 (1993) and 50.7 mg (0.2 mmol) placed in an oven dried flask (5 mL r.b.) containing $CH_2Cl_2$ (1 mL) and a magnetic stir bar. The flask was sealed with a rubber septum and the atmosphere was exchanged for nitrogen. The reaction mixture was cooled to −78° C. and a $BBr_3$ solution (1 mL, 4.3 equiv, 1M in $CH_2Cl_2$) was added via syringe. The reaction mixture was immediately allowed to warm to room temperature and stir. After 10 h, the flask was cooled to −78° C. and carefully quenched with 1.5 mL of MeOH. The stir bar was removed and the reaction mixture was concentrated in vacuo to yield a brown oil. MeOH (3.5 mL) was added to dissolve the oil and the reaction mixture was concentrated again. This quenching procedure was repeated 6–8 times until the hydrobromide salt 101 (62.8 mg, 100%) was isolated as brown crystals; $^1H$ NMR (500 MHz, $CD_3OD$): δ6.23 [d, J=1.8 Hz, Ar—H(7)], 6.12 [d, J=2.1 Hz, Ar—H(5)], 4.64 [q, J=6.7 Hz, C$\underline{H}$CH$_3$], 3.75 [ddq, J=11.6, 4.6 and 6.5 Hz, CH$_2$C$\underline{H}$CH$_3$], 2.98 [dd, J=17.4 and 4.6 Hz, CH$_{ax}$$\underline{H}_{eq}$CHCH$_3$ ], 2.75 [dd, J=17.4 and 11.6 Hz, C$\underline{H}_{ax}$H$_{eq}$CHCH$_3$], 1.59 [d, J=7.0 Hz, CHC$\underline{H}_3$], and 1.46 [d, J=6.4 Hz, CH$_2$CHC$\underline{H}_3$]; $^{13}C$ NMR (125 MHz, $CD_3OD$): δ158.97, 156.10, 133.65, 112.61, 107.01, 101.94, 49.35, 45.35, 34.59, 19.23, and 18.33; m.p. (range): 140°–143°; Anal. Calcd for $C_{11}H_{16}NO_2Br$: C, 48.19; H, 5.88. Found: C, 48.35; H, 5.69.

EXAMPLE 2

Preparation of Tribenzylprotected Tetrahydroisoquinoline (102)

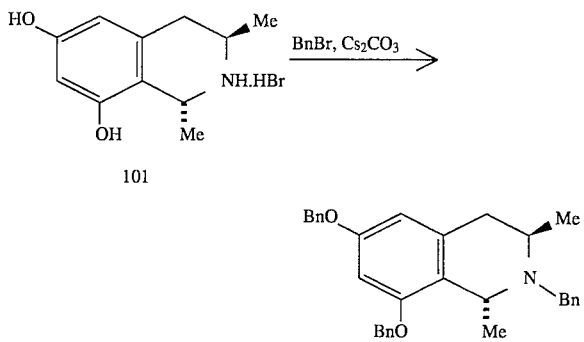

To a stirred solution of 1(R), 3(R)-1,2,3,4-tetrahydro-6,8-dihydroxy-1,3-dimethyl-isoquinoline hydrobromide salt (0.39 g, 1.4 mmol) in 15 mL of dry DMF was added benzylbromide (1.70 g, 10.0 mmol), followed by the addition of cesium carbonate (2.40 g, 7.4 mmol). After being stirred for 6 h at room temperature, the reaction mixture was poured into $H_2O$ (100 mL), and EtOAc (100 mL) was added. The organic layer was washed with brine, dried over $Na_2SO_4$, and concentrated in vacuo. The residue was purified by flash chromatography (hexanes/EtOAc/$Et_3N$; 9:1:0.1) to yield tribenzyl-protected tetrahydroisoquinoline 102 (0.57 g, 86%) as a thick yellow oil.; $^1H$ NMR (500 MHz, CDCl$_3$): δ7.42–7.21 [m, benzyl ArH], 6.42 [d, J=2.0 Hz, ArH(7)], 6.34 [d, J=2.0 Hz, ArH(5)], 4.99 [s, O(6)CH$_2$Ph], 4.98 [d, J=12.0 Hz, O(8)CH$_a$$\underline{H}_b$Ph], 4.95 [d, J=12.0 Hz O(8)C$\underline{H}_a$H$_b$Ph], 4.01 [q, J=7.0 Hz, ArC$\underline{H}$CH$_3$], 3.82 [d, J=14.0 HZ, NC$\underline{H}_a$H$_b$Ph], 3.52 [ddq, J=10.5, 4.5 and 6.5 Hz, CH$_a$CH$_b$C$\underline{H}$], 3.32 [d, J=14.0 Hz, NCH$_a$$\underline{H}_b$Ph], 2.63 [dd, J=17.0 and 10.5 Hz, C$\underline{H}_a$CH$_b$CH ], 2.58 [dd, J=17.0 and 4.5 Hz, CH$_a$C$\underline{H}_b$CH], 1.34 [d, J=6.5 Hz, CH$_3$(1)], and 1.26 [d, J=6.5 Hz, CH$_3$(3)]; $^{13}C$ NMR (75 MHz, CDCl$_3$): δ157.6, 157.1, 137.1, 136.7, 129.0, 128.7, 128.5 [5C], 128.4 [2C], 128.3, 128.0 [2C], 127.9, 127.6 [2C], 126.9 [2C], 126.4, 105.5, 98.3, 70.0, 69.6, 51.2, 50.0, 45.7, 32.6, 19.9, and 19.5; IR (neat NaCl plates): 2967, 1603, 1454, and 1149 cm$^{-1}$; Anal. calcd for $C_{32}H_{33}NO_2$: C, 82.90; H, 7.17. Found: C, 82.89; H, 6.95.

EXAMPLE 3

Preparation of Iodide (8)

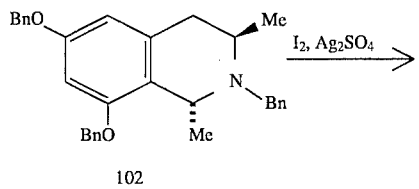

102

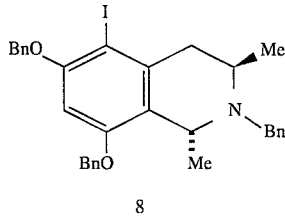

8

A solution of compound 102 (0.48 g, 1.0 mmol) in 10 mL of EtOH and 2 mL of CH$_2$Cl$_2$ was added slowly to a stirred mixture of iodine (0.53 g, 2.1 mmol) and silver sulfate (0.69 g, 2.2 mmol) in 10 mL of EtOH. After being stirred at room temperature for 16 h, the yellow solid was removed by filtration and the filtrate was concentrated in vacuo. The resulting residue was dissolved in CH$_2$Cl$_2$ (100 mL). This solution was washed with saturated NaHCO$_3$, H$_2$O, dried over Na$_2$SO$_4$, and concentrated in vacuo. The residue was purified by flash chromatography (hexanes/EtOAc; 9:1) to yield iodide 8 (0.40 g, 66%) as a thick oil; $^1$H NMR (500 MHz, CDCl$_3$): δ7.49–7.18 [m, benzyl ArH], 6.41 [s, ArH(7)], 5.07 [s, O(6)CH$_2$Ph], 4.98 [d, J=12.0 Hz, O(8)CH$_a$H$_b$Ph], 4.94 [d, J=12.0 Hz, O(8)CH$_a$H$_b$Ph], 4.01 [q, J=6.5 Hz, CHCH$_3$], 3.82 [d, J=14.0 Hz, NCH$_a$H$_b$Ph], 3.51 [ddq, J=12.0, 4.0 and 6.5 Hz, CH$_a$H$_b$CHCH$_3$], 3.20 [d, J=14.0 Hz, NCH$_a$H$_b$Ph], 2.66 [dd, J=17.5 and 4.0 Hz, CH$_a$H$_b$CH], 2.42 [dd, J=17.5 and 12.0 Hz, CH$_a$CH$_b$CH], 1.34 [d, J=6.5 Hz, CH$_3$(1)], and 1.31 [d, J=6.5 Hz CH$_3$(3)]; $^{13}$C NMR (75 MHz, CDCl$_3$): δ157.4, 156.1, 141.3, 139.5, 137.1 [2C], 128.9 [7C], 128.5 [2C], 128.2, 127.4 [2C], 127.2 [3C], 126.9, 124.3, 97.7, 71.6 70.3, 51.9, 50.1, 46.9, 39.3, 20.2, and 20.1; IR (neat NaCl plates): 2971, 1585, 1324, and 1062 cm$^{-1}$; Anal. calcd for C$_{32}$H$_{32}$INO$_2$: C, 65.20; H, 5.47. Found: C, 65.39; H, 5.73.

EXAMPLE 4

Preparation of 5-Bromo-(1R, 3R)-1,2,3,4-tetrahydro-6,8-dimethoxy-1,3-dimethylisoquinoline (103)

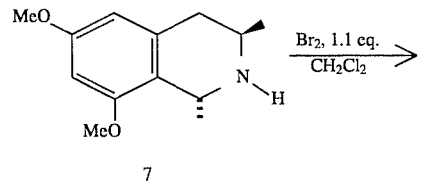

7

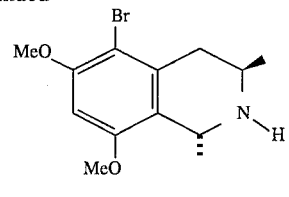

103

To a solution of tetrahydroisoquinoline 7 (50.0 mg, 0.23 mmol) in CH$_2$Cl$_2$ (0.5 ml) was added Br$_2$ (13 μL, 0.25 mmol). After stirring for 10 min the reaction was diluted with Et$_2$O, washed successively with saturated K$_2$CO$_3$, saturated Na$_2$S$_2$O$_3$, and brine. The organics were then dried over 4 A molecular sieves, filtered, and concentrated in vacuo. The resulting residue was triturated with Et$_2$O and a white solid was filtered (18.4 mg, 27% of brominated tetrahydroisoquinoline 103 as, the HBr salt) The remaining material was purified by MPLC (hexanes/EtOAc; 1:1 with 3% Et$_3$N) to yield an additional quantity (39.4 mg, 57%) of the brominated species (84% total); $^1$H NMR (200 MHz, CDCl$_3$): δ9.6 [vds, 1H, NH], 6.39 [s, Ar—H(7)], 4.84 [q, J=6.7 Hz, CHCH$_3$], 3.88 [s, OMe], 3.85 [s, OMe], 3.73 [ddq, J=11.6, 4.5, and 6.2 Hz, CH$_2$CHCH$_3$], 3.19 [dd, J=17.7 and 4.5 Hz, CHaH$_b$CHCH$_3$], 2.92 [dd, J=17.7 and 11.6 Hz, CHa H$_b$CHCH$_3$], 1.81 [d, J=6.2 Hz, CH$_2$CHCH$_3$], and 1.70 [d, J=6.7 Hz, CHCH$_3$]; LRMS (EI): m/z 298 (M$^+$–1,<1), 286 (97), 284 (100), 269, 256, 226, 204, 190, 176, 162, 147, 131, 103, 91, 77, 51, and 42 (all<5).

EXAMPLE 5

Preparation of N-benzyl-(1R, 3R)-1,2,3,4-tetrahydro-6,8-dimethoxy-1,3-dimethylisoquinoline (104)

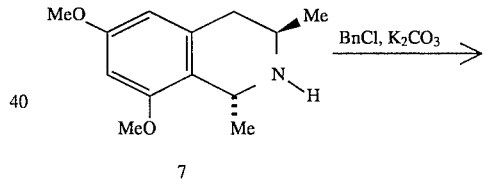

7

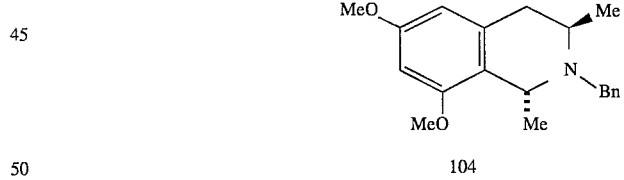

104

Into a stirred solution of (1R, 3R)-1,2,3,4-tetrahydro-6,8-dimethoxy-1,3-dimethyl-isoquinoline (114 mg, 0.5 mmol) and benzyl chloride (137 mg, 1.1 mmol) in methyl ethyl ketone was added K$_2$CO$_3$ (320 mg, 2.3 mmol). The resulting mixture was heated to reflux for 24 h, after which time it was cooled down and poured into H$_2$O. Et$_2$O was added and the organic layer was washed with H$_2$O, brine, dried over MgSO$_4$, and concentrated in vacuo. The crude product was purified by MPLC (hexanes/EtOAc/Et$_3$N; 9:1:0.3) to yield N-benzyl-(1R, 3R)- 1,2,3,4-tetrahydro-6,8-dimethoxy-1,3-dimethyl-isoquinoline (148 mg, 93%) as a colorless oil; $^1$H NMR (500 MHz, CDCl$_3$): δ7.40–7.20 [m, benzyl ArH], 6.28 [d, J=2.0 Hz, ArH(7)], 6.23 [d, J=2.0 Hz, ArH(5)], 3.66 [q, J=6.5 Hz, ArCHCH$_3$], 3.82 [d, J=14.0 Hz, NCH$_a$H$_b$Ph], 3.78 [s, O(6)CH$_3$], 3.70 [s, O(8)CH$_3$, 3.50 [ddq, J=10.5, 5.0 and 6.5 Hz, CH$_a$H$_b$CHCH$_3$], 3.29 [d, J=14.0 Hz, NCH$_a$H$_b$ Ph], 2.63 [dd, J=17.0 and 10.5 Hz, CH$_a$H$_b$CH], 2.58 [dd, J=17.0 and 5.0 Hz, CH$_a$H$_b$CH], 1.30 [d, J=6.5 Hz, CH$_3$(1)], and 1.25 [d, J=6.5 Hz, CH$_3$(3)]; $^{13}$C NMR (75 MHz, CDCl$_3$): δ158.5, 158.4, 141.7, 136.8, 128.4 [2C], 128.1 [3C], 126.4, 104.1, 96.4, 55.2, 55.1, 51.4, 49.8, 45.8, 32.6, 20.0, and 19.5; LRMS (EI): m/z 296 (M$^+$—CH$_3$, 100), and 91 (44); IR (neat NaCl plates): 2965, 1605, and 1148 cm$^{-1}$; Anal. calcd for C$_{20}$H$_{25}$NO$_2$: C, 77.14; H, 8.09. Found: C, 77.30; H, 8.06.

EXAMPLE 6

Preparation of N-benzyl-(1R, 3R)-1,2,3,4-tetrahydro-6,8-dihydroxy-1,3-dimethylisoquinoline hydrobromide salt (105)

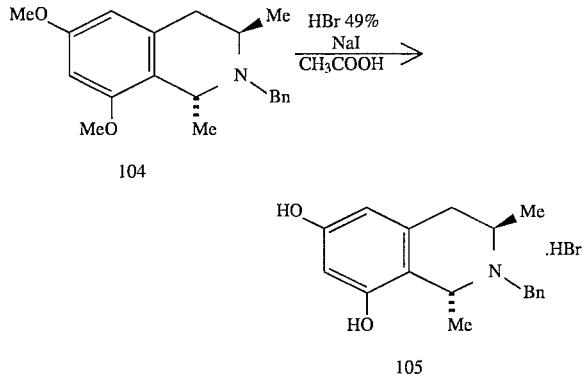

Into a 15 mL culture tube was placed N-benzyl-(1R, 3R)-1,2,3,4-tetrahydro-6,8-dimethoxy-1,3-dimethylisoquinoline (62 mg, 0.2 mmol) dissolved in acetic acid (1 mL). To this solution were added sodium iodide (120 mg, 0.8 mmol) and concentrated aqueous hydrobromic acid (49%, 2 mL). The mixture was heated at 100° C. for 3 hours and then cooled to 0° C., at which time light yellow crystals precipitated out of solution. Vacuum filtration with a glass fritted Buchner funnel gave the N-benzyl-(1R, 3R)-1,2,3,4-tetrahydro-6,8-dihydroxy-1,3-dimethyl-isoquinoline hydrobromide salt [105] (48 mg, 66%) as light yellow crystals.

EXAMPLE 7

Preparation of N-benzyl-(1R,3R)-5-bromo- 1,2,3,4-tetrahydro-6,8-dimethoxy-1,3-dimethylisoquinoline (106)

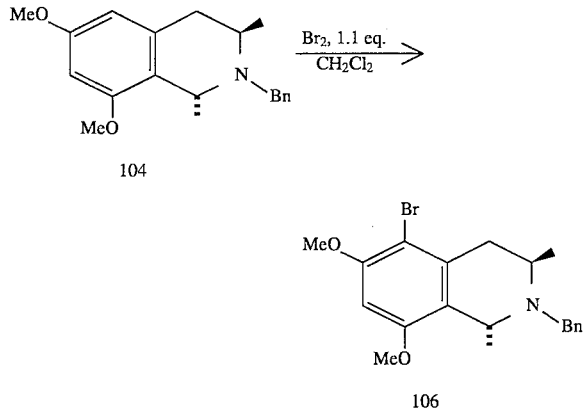

Into a 25 mL round bottom flask was placed N-benzyl-(1R, 3R)-1,2,3,4-tetrahydro-6,8-dimethoxy-1,3-dimethylisoquinoline (288 mg, 0.9 mmol) dissolved in methylene chloride (3 mL). Bromine (156 mg, 1.0 mmol) in methylene chloride (1 mL) was added to the solution. The mixture was stirred for 3 h at room temperature and then diluted with methylene chloride (20 mL) and washed with H$_2$O (2×5 ml). The organic layer was dried with sodium sulfate and concentrated in vacuo to yield 360 mg of crude material. Separation on MPLC (hexane/ethyl acetate; 9:1, 3% Et$_3$N) gave N-benzyl-(1R, 3R)-5-bromo-1,2,3,4-tetrahydro-6,8-dimethoxy-1,3-dimethylisoquinoline [106] (282 mg, 78%) as light yellow oil; $^1$H-NMR (CDCl$_3$, 200 MHz): δ7.31 [m, 5H, Ph], 6.4 [s, Ar-H(7)], 3.97 [q, J=6.6 Hz, CHCH$_3$], 3.91 [s, OMe] 3.84, [d, J=14.4 Hz, CH$_c$H$_d$Ph], 3.76 [s, OMe], 3.52 [ddq, J=11.6, 6.0, and 4.6 Hz, CH$_2$CHCH$_3$], 3.19 [d, J=14.4 Hz, CH$_c$H$_d$PH], 2.74 [dd, J=17.7 and 4.6 Hz, CH$_a$H$_b$CHCH$_3$], 2.45 [dd, J=17.7 and 11.6 Hz, CH$_a$H$_b$CHCH$_3$], 1.35 [d, J=6.0 Hz, CH$_2$CHCH$_3$], and 1.31 [d, J=6.6 Hz, CHCH$_3$]; $^{13}$C-NMR (CDCl$_3$, 200 MHz): δ157.0, 154.4, 140.9, 136.1, 128.3 [2C], 128.0 [2C], 126.3, 122.1, 104.5, 94.3, 56.3, 55.3 [2C], 51.3, 49.4, 45.7, 33.1, and 19.8; LRMS (EI): m/z 374 (M$^+$–15, 70), 360, 294, 268, 226, 203, 190, 162, 145 (all <5), 91 (100), 65, and 39.

EXAMPLE 8

Preparation of Iodide (107)

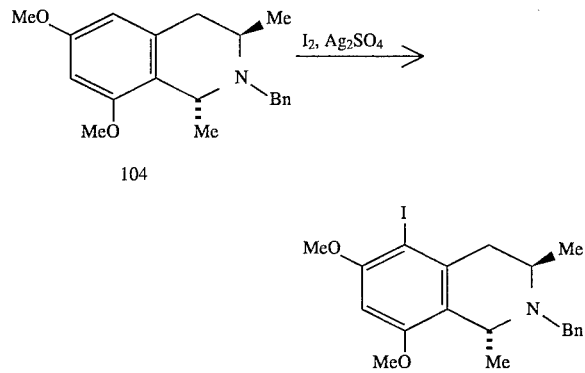

A solution of N-benzyl-(1R, 3R)-1,2,3,4-tetrahydro-6,8-dimethoxy-1,3-dimethyl-isoquinoline (198 mg, 0.61 mmol) in 5 mL of EtOH was added slowly to a stirred mixture of iodine (333 mg, 1.3 mmol) and silver sulfate (468 mg, 1.5 mmol) in 10 mL of EtOH. After being stirred at room temperature overnight, the yellow solid was removed by filtration and the filtrate was concentrated in vacuo. The resulting residue was dissolved in 40 mL of CH$_2$Cl$_2$. The solution was washed with saturated NaHCO$_3$, H$_2$O, dried over Na$_2$SO$_4$, and concentrated in vacuo. The crude, product was purified by flash chromatography (hexanes/EtOAc; 9:1) to yield iodide 107 (200 mg, 75%) as a white solid; $^1$H NMR (500 MHz, CDCl$_3$): δ7.35–7.20 [m, 5H, Ph], 6.36 [s, ArH(7)], 3.90 [q, J=6.5 Hz, ArCHCH$_3$], 3.89 [s, O(6)CH$_3$], 3.81 [d, J=14.5 Hz, NCH$_a$H$_b$Ph], 3.75 [s, O(8)CH$_3$], 3.49 [ddq, J=11.5, 4.5 and 6.5 Hz, CH$_a$H$_b$CHCH$_3$], 3.16 [d, J=14.5 Hz, NCH$_a$ H$_b$Ph], 2.63 [dd, J=17.5 and 4.5 Hz, CH$_a$H$_b$CH], 2.39 [dd, J=17.5 and 11.5 Hz, CH$_a$H$_b$CH], 1.33 [d, J=6.5 Hz, CH$_3$(1)], and 1.29 [d, J=6.5 Hz, CH$_3$(3)]; $^{13}$C NMR (75MHz, CDCl$_3$): δ158.5, 156.8, 141.1, 139.1, 128.4 [2C], 128.1 [3C], 126.4, 123.2, 94.0, 56.6, 55.3, 51.7, 49.6, 46.6, 38.7, 19.9, and 19.8; IR (neat NaCl plates): 2966, 1586, 1453, 1326, 1207, and 1072 cm$^{-1}$.

EXAMPLE 9

Preparation of 2,4-Dibromo-1-methoxymethoxybenzene (9)

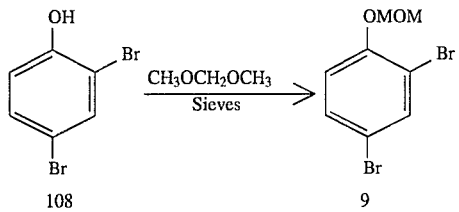

Into a 500-mL round bottom flask equipped with a soxlet and a condensor were placed 2,4-dibromophenol (32.0 g, 0.13 mole), dimethoxymethane (200 mL, 2.26 mole), p-toluenesulfonic acid monohydrate (2.24 g, 12.0 mmol) and $CH_2Cl_2$ (200 mL). The soxlet extractor was filled with 3 A and 4 A molecular sieves. The reaction mixture was heated to reflux for 24 h after which time the soxlet extractor was filled with freshly activated sieves. The reaction mixture was heated to reflux for another 24 h. After this period of time, $Et_3N$ (10 mL) was added. The reaction mixture was stirred for 5 mn, and concentrated to dryness. The residue was dissolved in $CH_2Cl_2$ (400 mL) and the resulting solution was washed with 5% NaOH (400 mL), $H_2O$ (400 mL), dried over $Na_2SO_4$, and concentrated in vacuo. The crude product was purified by flash chromatography (hexanes/EtOAc; 6:1) to yield 2,4-Dibromo-1-methoxymethoxybenzene [9](32.9 g, 88%) as a light yellow oil; $^1H$ NMR ($CDCl_3$, 300 MHz) δ7.67 [s, ArH(3)], 7.33 [d, J=8.7 Hz, ArH(5)], 7.02 [d, J=8.7 Hz, ArH(6)], 5.21 [s, $OCH_2OCH_3$], and 3.49 [s, $OCH_3$]; LRMS (EI) m/z 298 ($M^+$, $\overline{3}$), 296 ($M^+$, 5), 294 ($M^+$, 3), and 45 (100)

EXAMPLE 10

Preparation of Naphthol (12)

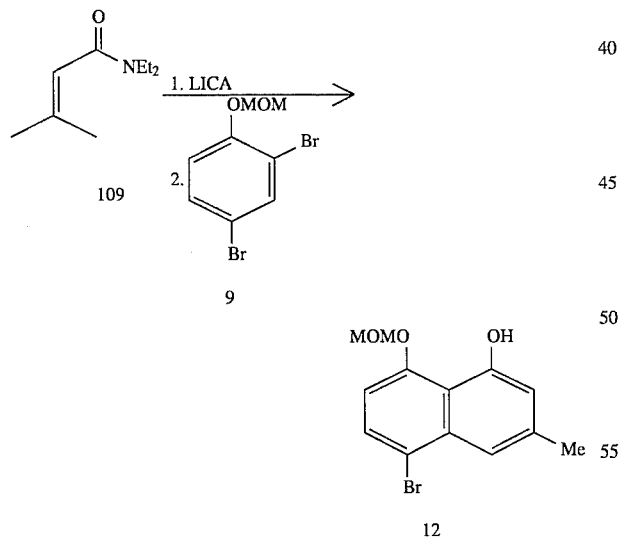

To a stirred solution of isopropylcyclohexylamine (7.5 mL, 0.45 mmol) in 60 mL of THF at −78° C. under $N_2$ was added n-BuLi (20.0 mL, 50.0 mmol, 2.5M in hexanes). The mixture was stirred for 20 min, warmed to 0° C., and then stirred for 1 h. The mixture was cooled to −78° C. and solution of N,N-diethyl-3,3-dimethylacrylamide (2.10 g, 13.0 mmol) in 40 mL of THF was added. This mixture was stirred at −78° C. for 1 h. The cold bath was removed and the reaction mixture was allowed to warm to −20° C. over a period of 10 min. A solution of 2,4-dibromo-1-methoxymethoxybenzene (9) in 30 mL of THF was added. The reaction mixture was stirred overnight at room temperature, and then quenched with saturated $NH_4Cl$ $Et_2O$ was added and the solution was washed with $H_2O$, brine, dried over $Na_2SO_4$, and concentrated in vacuo. The crude product was purified by flash chromatography (hexanes/EtOAc; 9:1) to yield napthol 12 (1.15 g, 29%) as a brown oil; $^1H$ NMR ($CDCl_3$, 300 MHz): δ9.31 [s, OH], 7.54 [d, J=8.4 Hz, ArH(6)], 7.49 [s, ArH(4)], 6.82 [s, ArH(2)[, 6.81 [d, J=8.4 Hz, ArH(7)], 5.46 [s, $OCH_2OCH_3$], 3.55 [s, $OCH_3$], and 2.47 [s, $ARCH_3(3)$]; $^{13}C$ NMR ($CDCl_3$, 75 MHz): 67 154.3, 153.5, 139.5, 134.5, 129.6, 118.2, 115.5, 114.5, 113.6, 107.3, 95.9, 56.9, and 22.0; LRMS (EI): m/z 298 ($M^+$, 13), 296 ($M^+$, 11), 128 (5), 115 (9), and 45 (100).

EXAMPLE 11

Preparation of Bromide (111)

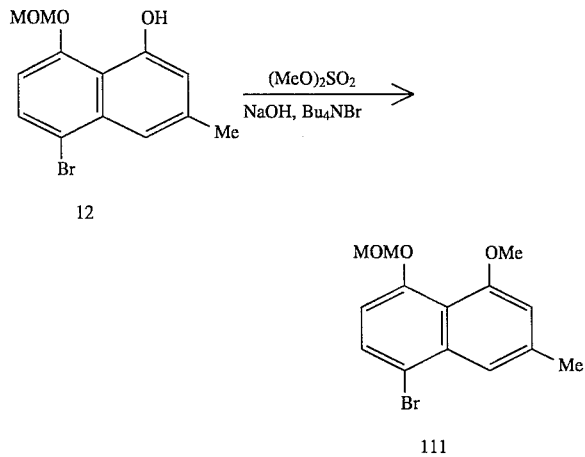

To a stirred solution of dimethyl sulfate (2.49 g, 20.0 mmol) in 20 mL of $CH_2Cl_2$ was added a solution of $Bu_4NBr$ (2.19 g, 6.8 mmol) and NaOH (0.50 g, 12.0 mmol) in 15 mL of $H_2O$ and a solution of naphthol 12 (1.07 g, 3.6 mmol) in 10 mL of $CH_2Cl_2$. The reaction mixture was stirred at room temperature for 18 h. The organic and aqueous layers were separated and the aqueous layer was extracted with 20 mL of $CH_2Cl_2$. The combined organic layers were washed with $H_2O$, dried over $Na_2SO_4$, and concentrated in vacuo. The crude product was purified by MPLC (hexanes/EtOAc; 9:1) to yield 111 (0.83 g, 74%) of as a white solid; $^1H$ NMR ($CDCl_3$, 300 MHz): δ7.63 [s, ArH(5)], 7.62 [d, J=8.1 Hz, ArH(3)], 6.86 [d, J=8.1 Hz, ArH(2)], 6.75 [s, ArH(7)], 5.22 [s, $OCH_2OCH_3$], 3.94 [s, ArO( 8)$CH_3$], 3.58 [s, $OCH_2OCH_3$], and 2.51 [s, $ARCH_3(6)$]; $^{13}C$ NMR ($CDCl_3$, 75 MHz): δ156.8, 154.0, 137.8, 135.0, 130.4, 119.5, 118.1, 115.3, 112.9, 109.3, 96.8, 56.5, 56.4, and 22.2; LRMS (EI): m/z 312 ($M^+$, 18), 310 ($M^+$, 19), 282 (15), 280 (16) 231 (2), 128 (14), and 45(100).

EXAMPLE 12

Preparation of Compound (113)

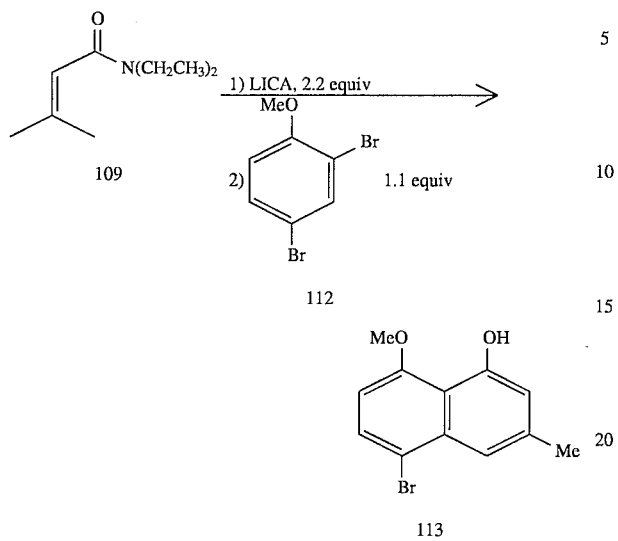

In a 250 mL round bottomed flask a solution of lithiumisopropylcyclohexylamide was prepared from isopropylcyclohexylamine (6.21 g, 7.23 mL, 44 mmol) in THF (50 mL) and butyllithium (2.5M in hexane, 17.6 mL, 44 mmol). The solution was cooled to −78° C. under nitrogen and N,N-diethyl-3,3-dimethylacrylamide [109] (3.10 g, 20 mmol) in THF (20 mL) was added. After stirring for 30 min at −78° C., the solution was warmed to room temperature and stirred for 5 h. The reaction mixture was then cooled to −78° C., and 1,4-dibromoanisole [112] (5.852 g, 22 mmol) in THF (30 mL) was added via syringe. The solution was stirred at 0° C. for 24 h and then quenched with saturated aqueous ammonium chloride (100 mL) and diluted with ether (30 mL). The organic layer was separated and the aqueous layer was extracted with ether (3×40 mL). The combined organic layers were washed with brine (40 mL), dried with sodium sulfate and concentrated in vacuo to give 4.60 g of crude material. Flash chromatography of the crude material (hexane/ethyl acetate; 9:1) yielded product 113 (1.17 g, 22%) as a light yellow oil.

EXAMPLE 13

Preparation of Compound (114)

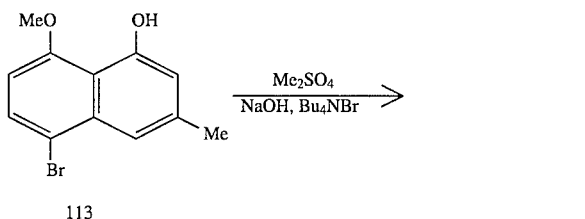

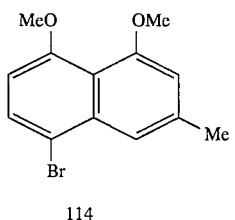

A solution of dimethyl sulfate (2.52 g, 20.0 mmol) in methylene chloride (20 mL) was prepared in a 100 mL round bottom flask. To the flask was added a solution of tetrabutylammonium bromide (2.25 g, 7.0 mmol) and sodium hydroxide (400 mg, 10.0 mmol) in water (15 mL). To this mixture was added a solution of compound 113 (1.335 g, 5 mmol) in methylene chloride (10 mL). The reaction mixture was stirred at room temperature for 18 h and then diluted with methylene chloride (20 mL). The organic and aqueous layers were separated, and the aqueous layer was extracted with of methylene chloride (20 mL). The combined organic layers were washed with water (10 mL), dried with sodium sulfate, and concentrated in vacuo. The resulting residue was purified by flash chromatography (hexane/ethyl acetate; 9:1) to obtain compound 114 (1.32 g, 94%) as a white solid.

EXAMPLE 14

Preparation of Compound (116)

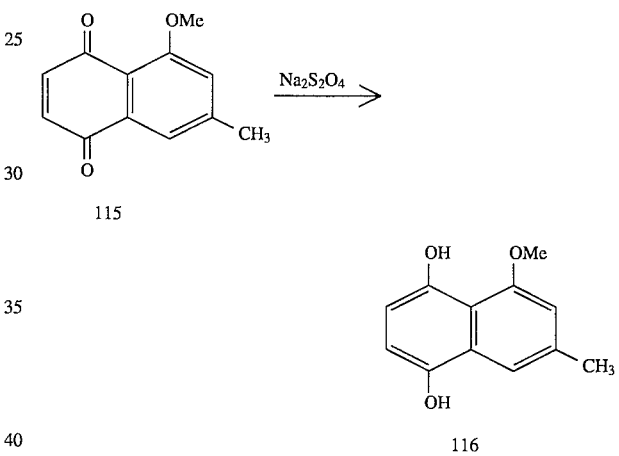

In a 100 mL round bottom flask, 7-methyl-Juglone [115] (242.4 mg, 1.2 mmol) was dissolved in chloroform (30 mL). Water (15 mL) and sodium dithionite (627 mg, 3.6 mmol) were added to this and the mixture was stirred at room temperature for 1 h. When TLC analysis showed no starting material remaining, the organic layer was separated, washed with brine, dried with sodium sulfate and concentrated in vacuo to yield compound 116 (245 mg, 100%) as a white solid.

EXAMPLE 15

Preparation of Compound (117)

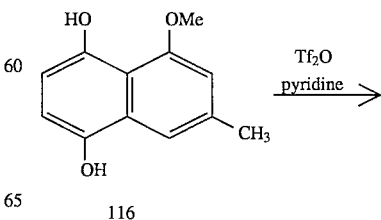

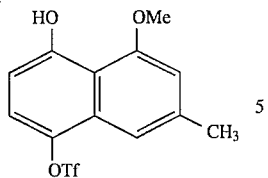

117

Compound 116 (204 mg, 1.0 mmol) was placed in a 50 mL round bottom flask with methylene chloride (10 mL) and pyridine (0.32 mL, 4.0 mmol). The mixture was cooled to −5° C. and triflic anhydride (0.20 mL, 1.15 mmol) was added. The reaction mixture was stirred at room temperature for 12 h. Methylene chloride (20 mL) was added and the mixture was washed with water, dried with sodium sulfate and concentrated in vacuo. Purification by flash chromatography (Hexanes/ethyl acetate; 12:1) yielded product 117 (182 mg, 54%) as a white solid.

EXAMPLE 16

Preparation of Compound (118)

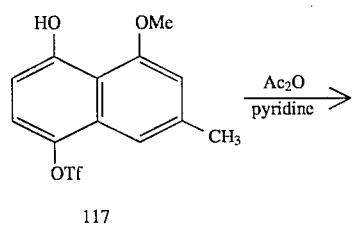

117

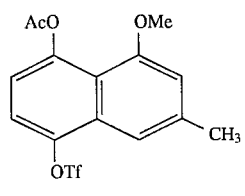

118

Into a 15 mL round bottom flask was placed monotriflate 117 (50 mg, 0.15 mmol) dissolved in methylene chloride (2 mL). To this solution was added acetic anhydride (0.04 mL, 0.45 mmol) and pyridine (0.072 mL, 0.90 mmol). The reaction mixture was stirred at room temperature for 9 h. When TLC analysis showed no remaining starting material, the mixture was diluted with methylene chloride (10 mL), washed with water, dried with sodium sulfate and concentrated in vacuo to give compound 118 (56 mg, 100%) as a white solid.

EXAMPLE 17

Preparation of Boronic Acid (13)

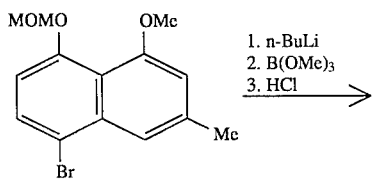

111

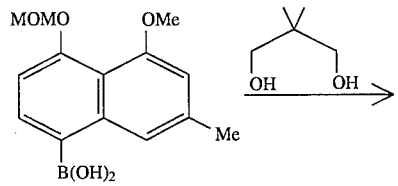

13

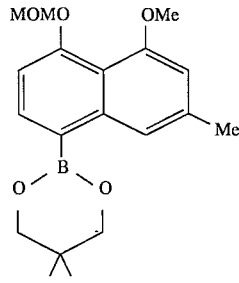

119

To a stirred solution of 111 (0.83 g, 2.7 mmol) in 30 mL of THF at −78° C. under $N_2$ was added n-BuLi (1.3 mL, 3.2 mmol, 2.5M in hexanes). The resulting mixture was stirred for 15 min and then cannulated into a solution of $B(OMe)_3$ (0.65 mL, 5.7 mmol) in 30 mL of THF. The reaction mixture was stirred for another 15 min, then warmed to room temperature and stirred for 2 h. The reaction mixture was quenched with 10 % HCl, diluted with $Et_2O$, washed with $H_2O$, brine, dried over $MgSO_4$, and concentrated in vacuo to yield boronic acid 13 (0.74 g, 100% as a brown solid. This compound was used without further purification. The structure of boronic acid [13] was confirmed by derivatization to boronate ester 119; GC: $t_R$=13.3 min; column: DB-5,6 m×0.1 mm×0.1 μm film; temp prom: 50° C./2 min/20° C. $min^{-1}$/250° C./10 min: LRMS (EI): m/z 344 ($M^+$, 100), 314 (46), 300 (20), 270 (17), and 45 (75).

EXAMPLE 18

Preparation of Boronic Anhydride (120)

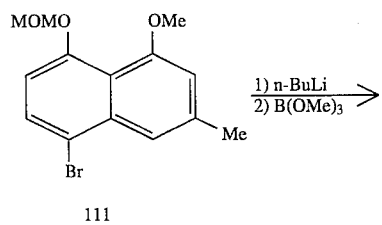

111

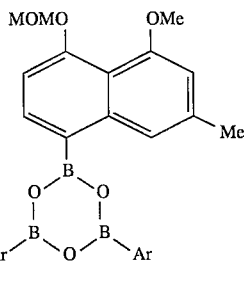

120

Into a 25 mL flame dried flask was placed bromide 111 (1.10 g, 3.54 mmol) freshly distilled THF (10 mL). Under nitrogen, the solution was cooled to −78° C. and then n-butyllithium (2.5M in hexane, 1.7 mL, 4.2 mmol) was added. The resulting solution was stirred for 15 minutes, after which time a precipitate appeared. Trimethyl borate (1.7 mL, 14.4 mmol) was added to the flask and a clear solution formed. The mixture was stirred at −78° C. for 30 min and then at room temperature for 2 h. The mixture was quenched with saturated aqueous ammonium chloride (10 mL), concentrated, and diluted with of methylene chloride (20 mL). The organic and aqueous layers were separated and the aqueous layer was neutralized with 10% aqueous hydrochloric acid. The aqueous layer was extracted with methylene chloride (2×20 mL), and the combined organics were washed with $H_2O$ (10 mL) and dried over sodium sulfate. Concentration in vacuo yielded 1.0 g of crude material as a caramel colored residue. Precipitation from methylene chloride by addition of hexanes gave the anhydride 120 (548 mg, 60%) as a white solid; $^1$H-NMR (CDCl$_3$, 300MHz): δ8.72: [s, ArH(1)], 8.52 [s, J=7.7 Hz, ArH(7)], 7.08 [d, J=7.8 Hz, ArH(6)], 6.76 [s, ArH(3)], 5.37 [s, OCH$_2$OCH$_3$], 3.97 [s,ArOCH$_3$], 3.62 [s, OCH$_2$O̲CH$_3$], and 2.43[s, ARCH$_3$].

EXAMPLE 19

General Procedure for the Palladium(0)-Mediated Biaryl Coupling Reactions

To a stirred solution of aryl iodide in toluene (0.05M) was added 2 equivalents of boronic acid (or its derivatives). Saturated NaHCO$_3$ (½ volume of toluene) was then added, followed by the addition of 20 mol % of Pd(PPh$_3$)$_4$. The reaction mixture was sealed under N$_2$ in a culture tube and heated to 110° C. for 20 h. After this period of time, EtOAc and brine were added. The organic layer was extracted, dried over Na$_2$SO$_4$, and concentrated in vacuo. The crude product was purified by silica gel chromatography.

A. Preparation of Compound (14)

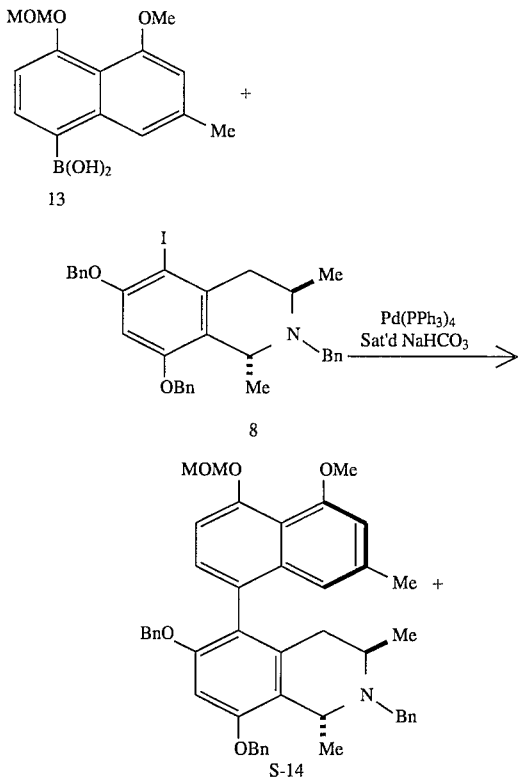

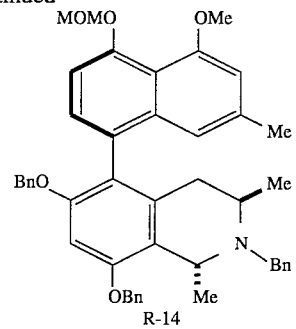

Compound 14 was obtained from boronic acid 13 and iodide 8 in 81% yield with a 4:3 ratio of S-14 to R-14. The product was purified by MPLC (hexanes/EtOAc/Et$_3$N; 3:1:0.1); $^1$H NMR of S-14 (500 MHz, CDCl$_3$): δ7.39–6.90 [m, ArH(6' and 7') and benzyl ArH], 6.77 [s, ArH(1')], 6.69 [s, ArH(3')], 6.53 [s, ArH(7)], 5.31 [s, OCH$_2$OCH$_3$], 5.02 [s, O(6)CH$_2$Ph], 4.87 [d, J=12.5 Hz O(8)CH̲$_a$H$_b$Ph], 4.81 [d, J=12.5 Hz, O(8)CH$_a$H̲$_b$Ph], 4.12 [q, J=6.5 Hz, PhCH̲CH$_3$], 3.98 [s, O(4')CH̲$_3$], 3.72 [d, J=14.5 Hz, NCH̲$_a$H$_b$Ph], 3.65 [s, OCH$_2$OCH$_{3+b}$], 3.37[ddq, J=11.5, 4.0, and 6.5 Hz, CH̲$_a$H$_b$CHCH$_3$], 3.30 [d, J=14.5 Hz, NCH$_a$H̲$_b$Ph], 2.36 [s, CH$_3$(2')], 2.22 [dd, J=17.5 and 4.0Hz, CH̲$_a$H̲$_b$CH], 2.00 [dd, J=17.5 and 11.5 Hz, CH$_a$H̲$_b$CH], 1.41 [d, J=6.5 Hz, CH$_3$(1)], and 1.01 [d, J=6.5 Hz, CH$_3$(3)]; $^1$H NMR of R-14 (500 MHz, CDCl$_3$): δ7.39–6.90 [m, ArH(6' and 7') and benzyl ArH], 6.86 [s, ArH(1')], 6.70 [s, ArH(3')], 6.51 [s, ArH(7)], 5.31 [s, OCH$_2$OCH$_3$], 5.03 [d, J=12.0 Hz, O(6)CH̲$_a$H$_b$Ph], 4.97 [d, J=12.0 Hz, O(6)CH$_a$H̲$_b$Ph], 4.86 [d, J=12.5 Hz, O(8)CH̲$_a$H$_b$Ph], 4.81 [d, J=12.5 Hz, O(8)CH$_a$H̲$_b$Ph], 4.11 [q, J=6.5 Hz, PhCH̲CH$_3$], 3.98 [s, O(4')CH$_3$], 3.77 [d, J=14.5 Hz, NCH̲$_a$H$_b$Ph], 3.65 [s, OCH$_2$OCH$_{3+b}$], 3.37 [ddq, J=14.0, 4.0, and 6.5 Hz, CH$_a$H$_b$CH̲CH$_3$ ], 3.35 [d, J=14.0 Hz, NCH$_a$H̲$_b$Ph], 2.36 [s, CH$_3$(2')], 2.25 [dd, J=17.0 and 14.0 Hz, CH̲$_a$H$_b$CH], 1.92 [dd, J=17.0 and 4.0 Hz, CH$_a$H̲$_b$CH], 1.39 [d, J=6.5 Hz, CH$_3$(1)], and 1.05 [d, J=6.5 Hz, CH$_3$(3)]; IR (neat NaCl plates): 2967, 1584, 1052, and 733 cm$^-$.

B. Preparation of Compound (121)

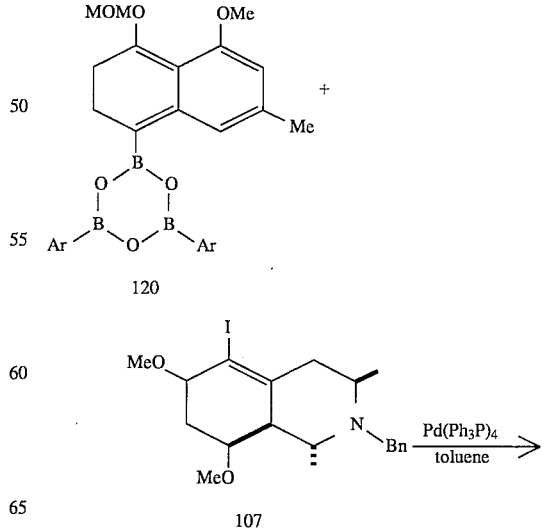

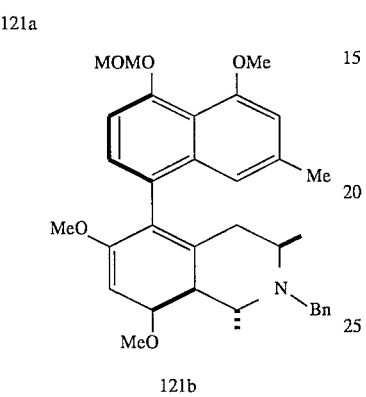

121a

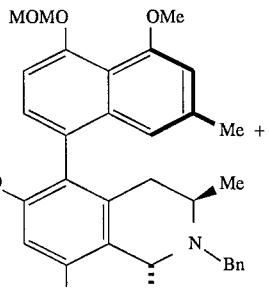

121b

Into a 15 mL culture tube were placed N-benzyl-(1R, 3R)-5-iodo- 1,2,3,4-tetrahydro-6,8-dimethoxy-1,3-dimethylisoquinoline [107] (66 mg, 0.15 mmol) and toluene (3 mL). To this solution was added compound 120 (58 mg, 0.23 mmol), which resulted in the formation of a slurry. A minimum amount of ethanol was added to change the slurry to a clear solution. To the resulting solution was added tetrakis(triphenylphosphine)palladium(0) (17 mg, 0.015 mmol) and saturated aqueous sodium bicarbonate (1.5 mL). The atmosphere was exchanged for $N_2$ and the reaction mixture was heated at 110° C. for 12 hours. When TLC showed no substrate boronate left, the organic and aqueous layers were separated and the aqueous layer was extracted with ethyl acetate (2×5 mL). The combined organics were washed with brine, dried over sodium sulfate and concentrated in vacuo. The resulting residue was purified by silica gel chromatography (hexane/ethyl acetate; 9:1, 3% $Et_3N$) to yield a mixture of compounds 121a and 121b (50 mg, 60% , as a white solid; $^1H$ NMR of 121a (500 MHz, $CDCl_3$): δ7.39–7.21 [m, benzyl ArH], 7.17 [d, J=8.0 Hz, ArH(7')], 7.07 [d, J=7.5 Hz, ArH(6')], 6.74 [s, ArH(1')], 6.68 [s, ArH(3')], 6.49 [s, ArH(7)], 5.31 [s, O$CH_2$O$CH_3$], 4.00 [q, J=6.5 Hz, N$C$H$CH_3$], 3.97 [s, O(4')$CH_3$], 3.85 [s O(6)$CH_3$], 3.72 [d, J=14.5, N$CH_aH_b$Ph], 3.65 [s, O(8)$CH_3$], 3.64 [s, O$CH_2$O$CH_{3+b}$], 3.36[ddq, J=11.0, 6.5 and 4.0 Hz, $CH_aH_b$ $C$H$CH_3$], 3.26 [d, J=14.0 Hz, N$CH_a$ $H_b$Ph], 2.35 [s, $CH_3$(2')], 2.12 [dd, J=17.5 and 4.0 Hz, $CH_aH_b$CH], 1.94 [dd, J=17.5 and 11.0 Hz, $CH_aH_b$CH], 1.38 [d, J=7.0 Hz, $CH_3$(1)], 1.00 [d, J=6.5 Hz, $CH_3$(3)]; $^1H$ NMR of 121b (500 MHz, $CDCL_3$): δ7.39–7.21 [m, benzyl ArH], 7.12 [d, J=8.0 Hz, ArH(7')], 7.06 [d, J=8.0 Hz, ArH(6')], 6.79 [s, ArH(1')], 6.69 [s, ArH(3')],6.48[s, ArH(7)], 5.30 [s, O$CH_2$O$CH_3$], 4.01 [q, J=6.5 Hz, N$C$H$CH_3$ ], 3.97[s, O(4') $CH_3$], 3.84 [s, O(6)$CH_3$], 3.76 [d, J=14.0 Hz, N$CH_aH_b$Ph], 3.65 [s, O(8)$CH_3$], 3.62]s, O$CH_2$O$CH_{3+b}$], 3.36[ddq, J =12.0, 6.5 and 4.5 Hz, $CH_aH_b$ $C$H$CH_3$ ], 3.31 [d, J=14.5 Hz, N$CH_aH_b$Ph], 2.35 [s, $CH_3$(2')], 2.17 [dd, J=18.0 and 12.0 Hz, $CH_aH_b$CH], 1.82 [dd, J=17.5 and 4.5 Hz, $CH_aCH_b$CH], 1.38 [d, J=7.0 Hz, $CH_3$(1)], 1.03 [d J=6.5 Hz, $CH_3$(3)].

EXAMPLE 20

General Procedure for the Hydrolysis Reactions

To a stirred solution of methoxymethyl-protected starting material in a mixed solvent (MeOH/$CH_2Cl_2$-10:1, 0.01M) was added 10N HCl (½₀ volume of solvent). The reaction mixture was stirred at room temperature for 16 h. After this period of time the solvent was evaporated. EtOAc and saturated $NaHCO_3$ were added. The organic layer was washed with brine, dried over $Na_2SO_4$, and concentrated in vacuo. The crude product was purified by chromatography.

A. Preparation of Compound (15)

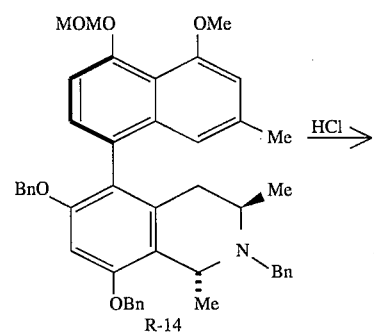

S-14

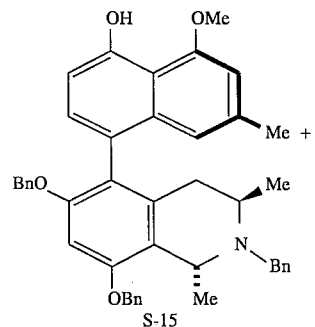

R-14

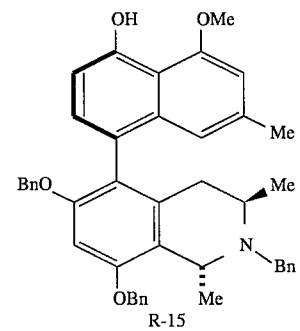

S-15

R-15

Compound 15 was obtained from compound 14 in 71% yield. The product was purified by MPLC (hexanes/

EtOAlEt$_3$N; 3:1:0.1); $^1$H NMR of S-15 (500 MHz, CDCl$_3$): δ9.40 [s, OH], 7.39–6.95 [m, ArH(7') and benzyl ArH], 6.91 [d, J=8.0 Hz, ArH(6')], 6.76 [s, ArH(1')], 6.62 [s, ArH(3')], 6.52 [s, ArH(7) ], 5.01 [s, O(6)CH$_2$Ph], 4.88 [d, J=13.0 Hz, O(8)CH$_a$H$_b$Ph], 4.82 [d, J=13.0 Hz O(8)CH$_a$H$_b$Ph], 4.08 [q, PhCHCH$_3$, hidden by O(4')CH$_3$], 4.08 [s, O(4')CH$_3$], 3.72 [d, J=14.0 Hz, NCH$_a$H$_b$Ph], 3.37 [ddq, J=11.5, 4.0, and 6.5 Hz, CH$_a$H$_b$CHCH$_3$], 3.29 [d, J=14.0 Hz, NCH$_a$H$_b$Ph], 2.36 [s, CH$_3$(2')], 2.21 [dd, J =17.5 and 4.0 Hz, CH$_a$H$_b$CH], 1.90 [dd, J=17.5 and 11.5 Hz, CH$_a$H$_b$CH], 1.40 [d, J=6.5 Hz, CH$_3$(1)], and 1.01 [d, J=6.5 Hz, CH$_3$(3)]; $^1$H NMR of R-15 (500 MHz, CDCl$_3$): δ9.42 [s, OH], 7.39–6.95 [m, ArH(7') and benzyl ArH], 6.90 [d, J=8.0 Hz, ArH(6')], 6.85 [s, ArH(1') 6.63 [s, ArH(3')], 6.50 [s, ArH(7)], 5.03 [d, J=115 Hz, O(6)CH$_a$H$_b$Ph], 4.97 [d, J=11.5 Hz, O(6)CH$_a$H$_b$Ph], 4.87 [d, J=13.0 Hz, O(8)CH$_a$H$_b$Ph], 4.82 [d, J=13.0 Hz, O(8)CH$_a$H$_b$Ph], 4.08 [q, PhCHCH$_3$, hidden by O(4')CH$_3$], 4.08 [s, O(4')CH$_3$], 3.77 [d, J=14.0 Hz, NCH$_a$H$_b$Ph], 3.37 [ddq, J=11.5, 4.0, and 6.5 Hz, CH$_a$H$_b$CHCH$_3$ ], 3.34 [d, J=14.0 Hz, NCH$_a$H$_b$Ph], 2.36 [s, CH$_3$(2')], 2.24 [dd, J=17.5 and 11.5 Hz, CH$_a$H$_b$CH], 1.90 [dd, J=17.5 and 4.0 Hz, CH$_a$H$_b$CH], 1.38 [d, J=6.5 Hz, CH$_3$(1)], and 1.05 [d, J=6.5 Hz, CH$_3$(3)].

B. Preparation of Compound (122)

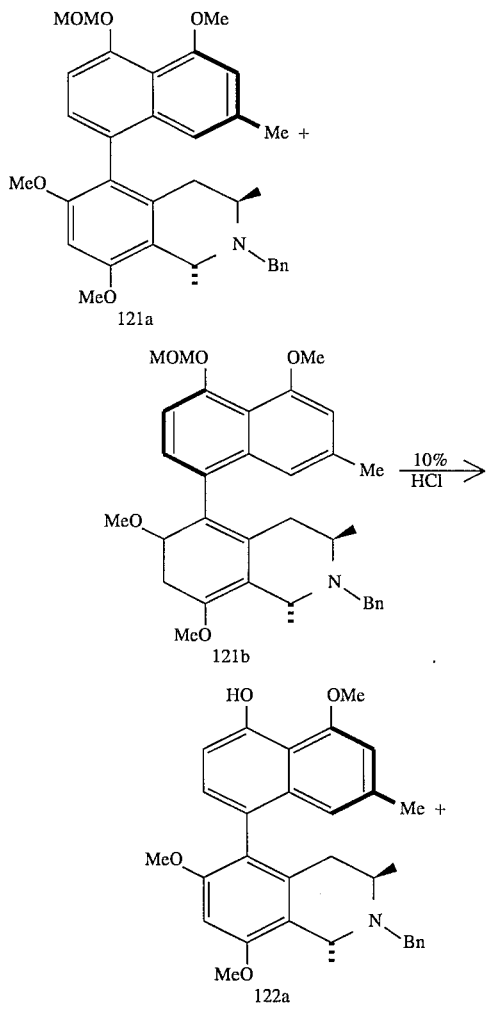

In a 10 mL round bottom flask, a mixture of substrates 121a and 121b (11 mg, 0.02 mmol) was dissolved in methanol (3 mL). To the solution was added 10% aqueous HCl (2 mL) and the reaction mixture was stirred at room temperature for 12 h. The reaction mixture was concentrated in vacuo and the resulting residue was dissolved in ethyl acetate (10 mL), washed with sodium bicarbonate, water, and dried over sodium sulfate. Concentration in vacuo yielded a mixture of compounds 122a and 122b (10 mg, 100%) as a white solid.

EXAMPLE 21

General Procedure for the Per-debenzylation Reactions

To a solution, of benzyl-protected monomer in a mixed solvent (MeOH/CH$_2$Cl$_2$-2:1.0.01M) was added 10% Pd/C (20 mol %). The atmosphere was exchanged for N$_2$, then H$_2$, and then a H$_2$ balloon was attached. The reaction mixture was stirred until TLC analysis indicated no starting material and possible intermediate left. The catalyst was removed by passing through a bed of Celite. The filtrate was concentrated in vacuo to yield deprotected monomer. The mixture of atropisomers was able to be separated by HPLC using an amino-bonded column.

A. Preparation of Korupensamine A & "C"

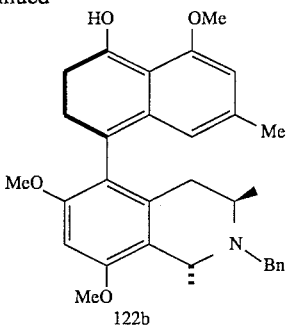

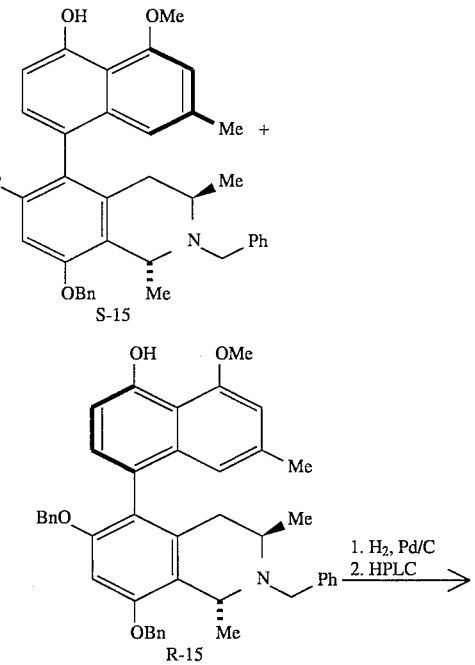

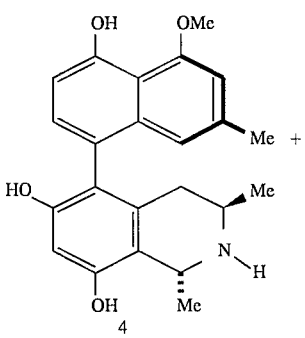

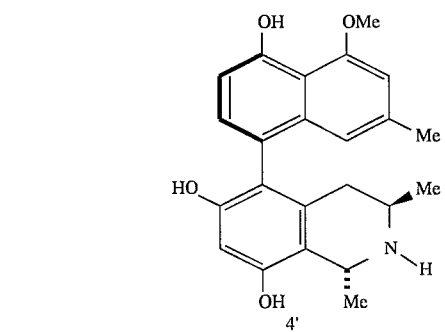

Compound 4 and 4' were obtained from compounds 15 in 75% yield. The atropisomers Korupensamine A [4] and "Korupensamine C" [4'] were separated by HPLC using an amino-bonded column (CHCl$_3$/MeOH/(NH$_4$)$_2$CO$_3$; 95:5:0.1); $^1$H NMR of 4 (HOAc Salt) (500 MHz, CD$_3$OD, referenced to CHD$_2$OD @ 3.30 ppm): δ7.09 [d, J=8.0 Hz, ArH(7')], 6.80 [d, J=8.0 Hz, ArH(6')], 6.78 [s, ArH(3')], 6.69 [s, Ar(1')], 6.44 [s, ArH(7)], 4.75 [q, J=7.0 Hz, ArCHCH$_3$], 4.08 [s, O(4')CH$_3$], 3.65 [ddq, J=12.0, 5.0 and 6.5 Hz, CH$_a$H$_b$CHCH$_3$], 2.62 [dd, J=18.0 and 5.0 Hz, CH$_a$H$_b$CH], 2.30 [s, CH$_3$(2')], 2.05 [dd, J=18.0 and 12.0 Hz, CH$_a$H$_b$CH], 1.64. [d, J=7.0 Hz, CH$_3$(1)], and 1.19 [d, J=6.5 Hz, CH$_3$(3)]; $^1$H NMR of 4' (HOAc Salt) (500 MHz, CD$_3$OD, referenced to CHD$_2$OD @ 3.30 ppm): δ7.02 [d, J=8.0 Hz, ArH(7')], 6.80 [d, J=8.0 Hz, ArH(6')], 6.80 [s, ArH(1or 3')], 6.78 [s, Ar(3' or 1')], 6.44 [s, ArH(7)], 4.74 [q, J=7.0 Hz, ArCHCH$_3$], 4.08 [s, O(4')CH$_3$], 3.62 [ddq, J=12.0, 5.0 and 6.5 Hz, CH$_a$H$_b$CHCH$_3$], 2.38 [dd, J=18.0 and 12.0 Hz, CH$_a$H$_b$CH], 2.33 [s, CH$_3$(2')], 2.23 [dd, J=18.0 and 5.0 Hz, CH$_a$H$_b$CH], 1.67 [d, J=6.5 Hz, CH$_3$(1)], and 1.23 [d, J=6.5 Hz, CH$_3$(3)].

EXAMPLE 22

General Procedure for the Silver Oxide Promoted Oxidative Coupling and Simultaneous Reductive Bleaching/Perdebenzylation Reactions To a stirred solution of benzyl-protected monomer in CH$_2$Cl$_2$ (0.01M) was added 5 equivalent of Ag$_2$O. The reaction mixture was stirred at room temperature in the dark for 40 h. The solid was removed by passing through the Celite bed. MeOH (volume equal to that of CH$_2$Cl$_2$) was added to the filtrate, followed by the addition of 10% Pd/C (20 mol %). The atmosphere was exchanged for N$_2$, then H$_2$, and then a H$_2$ balloon was attached. The reaction mixture was stirred until TLC analysis indicated no starting material and possible intermediate left. The catalyst was removed by passing through a bed of Celite. The filtrate was concentrated to yield deprotected dimer. The crude product was further purified by HPLC with amino-bonded column.

A. Preparation of Michellamines A, B, and C

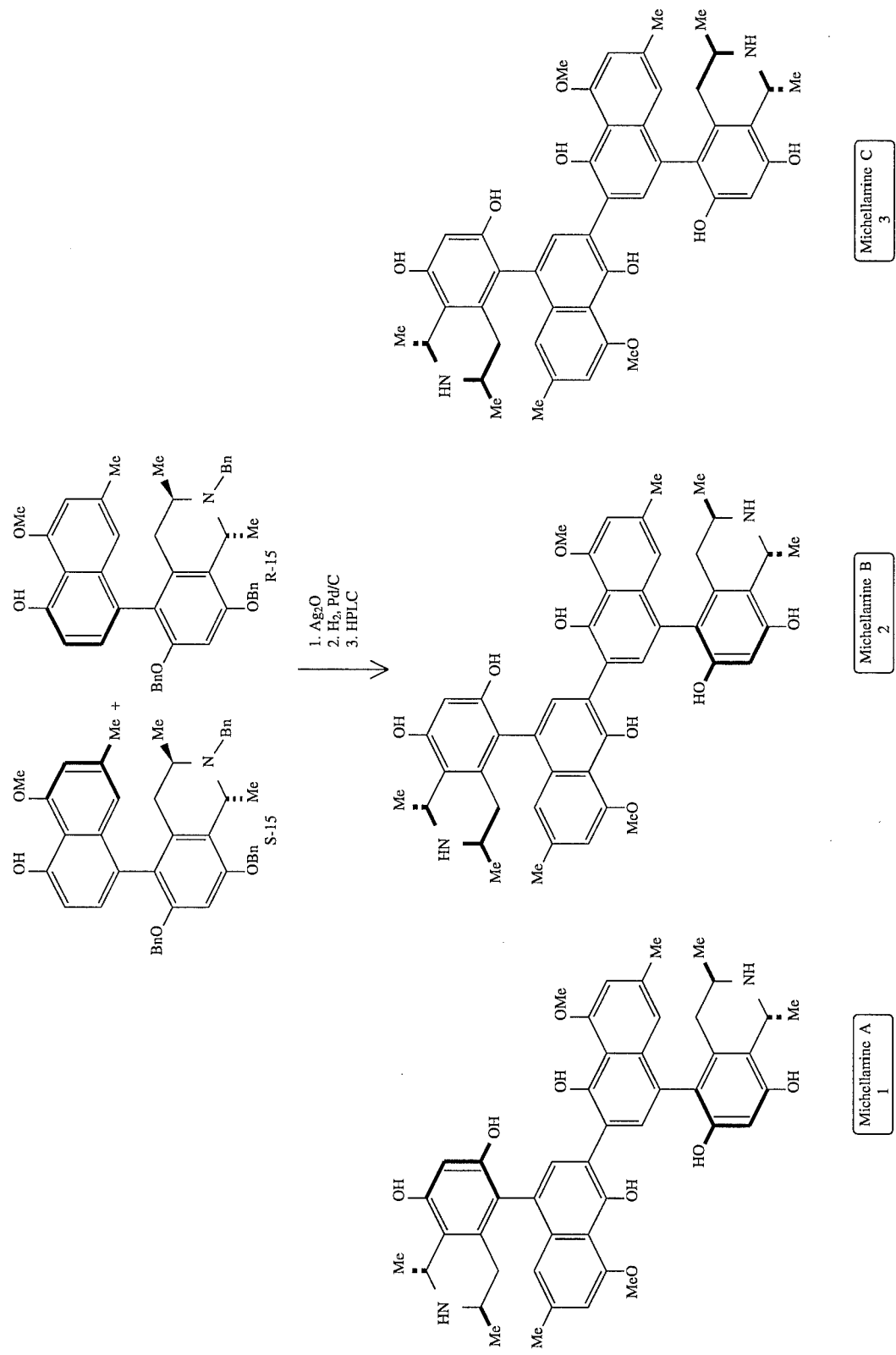

Michellamines A–C [1–3] were obtained from compound 15 in 90% yield. They were separated by HPLC using an amino-bonded column (CHCl$_3$/MeOH/(NH$_4$)$_2$CO$_3$; 93:7:0.1); $^1$H NMR of Michellamine A (1, HOAc Salt) (500 MHz, CD$_3$OD, referenced to CHD$_2$OD @3.30 ppm): δ7.30 [s, ArH(7')], 6.85 [s, ArH(3')], 6.74 [s, ArH(1')], 6.44 [s, ArH(7)], 4.77 [q, J=7.0 Hz, ArCHCH$_3$], 4.10 [s, O(4')CH$_3$], 3.70 [ddq, J=12.0, 4.5 and 6.5 Hz, CH$_a$H$_b$CHCH$_3$ ], 2.82 [dd, J=18.0 and 4.5 Hz, CH$_a$H$_b$CH], 2.34 [s, CH$_3$(2')], 2.15 [dd, J=18.0 and 12.0 Hz, CH$_a$H$_b$CH], 1.65 [d, J=6.5 Hz, CH$_3$(1)], and 1.24 [d, J=6.5 Hz, CH$_3$(3)]; $^1$H NMR of Michellamine B (2, HOAc Salt) (500 MHz, CD$_3$OD, referenced to CHD$_2$OD @ 3.30 ppm): δ7.32/7.27 [s, ArH(7')], 6.86/6.74 [s, ArH(3')], 6.85/6.83 [s, ArH(1')], 6.45 [s, ArH(7)], 4.76/4.73 [q, J=7.0/7.0 Hz, ArCHCH$_3$], 4.10/4.09 [s, O(4')CH$_3$], 3.73–3.62 [m, CH$_a$H$_b$CHCH$_3$], 2.79 [dd, J=17.5 and 5.0 Hz, CH$_a$H$_b$CH], 2.53 [dd, J=18.0 and 11.5 Hz, CH$_a$H$_b$CH], 2.36/2.33 [s, CH$_3$(2')], 2.34–2.29 [dd, CH$_a$H$_b$CH, hidden by CH$_3$(2')], 2.12 [dd, J=18.0 and 11.5 Hz, CH$_a$H$_b$CH], 1.69/1.64 [d, J=6.5/7.0 Hz, CH$_3$(1)], and 1.26/1.22 [d, J=6.0/6.5 Hz. CH$_3$(3)].

B. Preparation of Compounds (123a), (123b), and (123c)

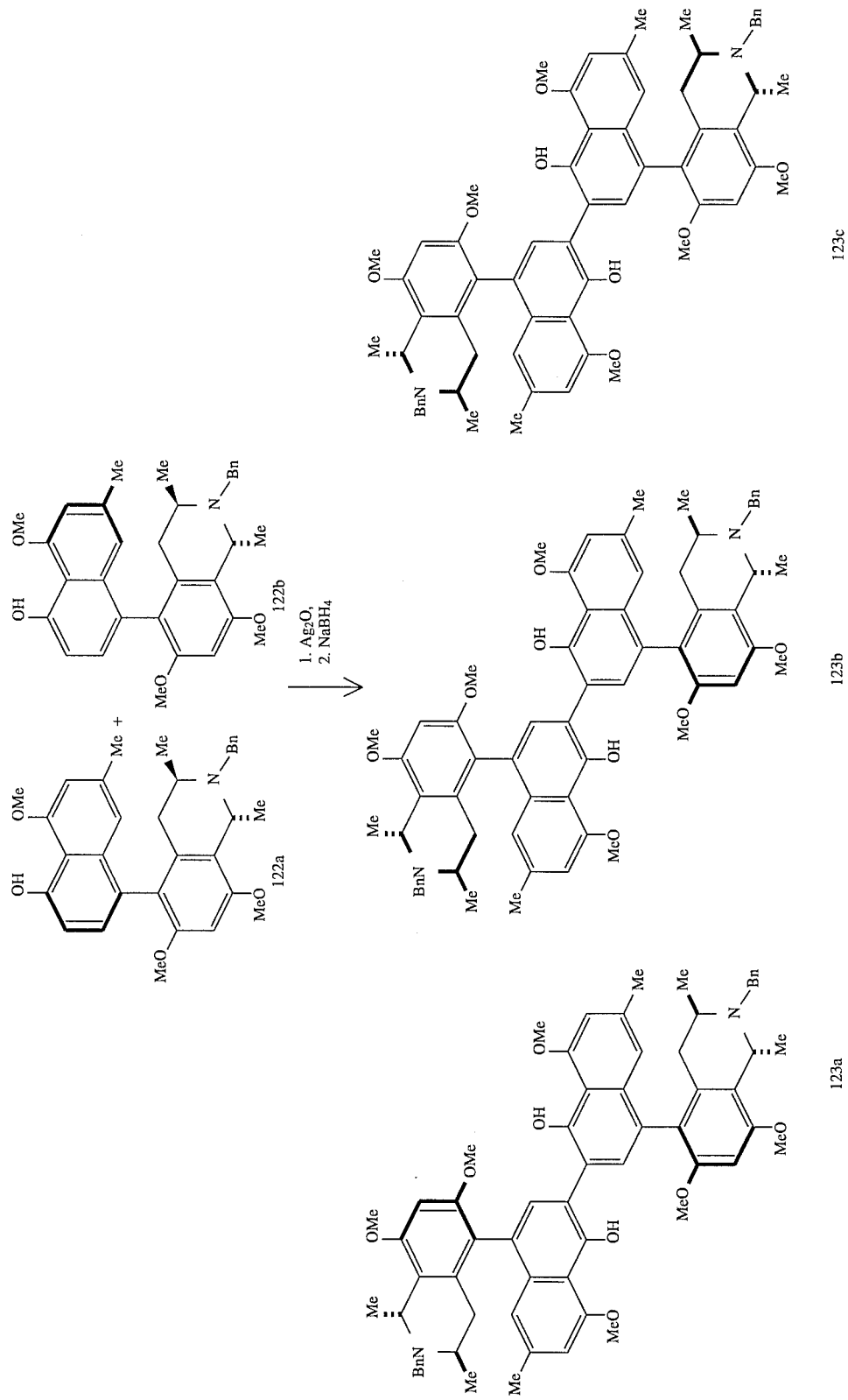

In a 10 mL round bottom flask, substrates 122a and 122b (5 mg, 0.01 mmol) were dissolved in methylene chloride (3 mL). To the solution was added silver (I) oxide (7 mg, 0.03 mmol) and the mixture was stirred at room temperature overnight. When TLC analysis showed no starting materials were left, the mixture was filtered through a bed of Celite bed. Concentration of the filtrate gave a blue solid (5 mg, 100%) which was dissolved in a mixed solvent of methylene chloride (2 mL) and methanol (2 mL). To the mixture was added a solution of $NaBH_4$ in methanol (2 mL). The mixture was concentrated, and the residue was dissolved in methylene chloride (10 mL), washed with water, and dried over sodium sulfate. Concentration in vacuo yielded a mixture of compounds 123a, 123b, and 123c (5 mg, 100%) as a white solid.

It will be appreciated by those skilled in the art that various modifications can be made to the above described embodiments of the invention without departing from the essential nature thereof. The invention is intended to encompass all such modifications within the scope of the appended claims.

What is claimed is:

1. A compound of the formula (I):

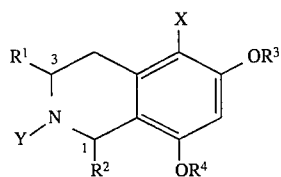

wherein X is Br, Cl or I, Y is H, $(C_1-C_4)$alkyl, benzyl, or CHO, each of $R^1$ and $R^2$ is H or $CH_3$, and each of $R^3$ and $R^4$ is H, benzyl, $(C_2-C_5)$acyl or an acid-labile hydroxy protecting group.

2. The compound of claim 1 wherein each of $R^3$ and $R^4$ is an acid-labile hydroxy protecting group.

3. The compound of claim 2 wherein the acid labile protecting group is $(C_1-C_4)$alkoxy$(C_1-C_4)$alkyl, tetrahydropyranyl, or $(R^8)_3Si$, wherein each $R^8$ is $(C_1-C_4)$alkyl.

4. The compound of claim 1 wherein $R^3$, $R^4$ and Y are the same protecting group.

5. The compound of claim 4 wherein $R^3=R^4=Y=$benzyl.

6. The compound of claim 5 wherein $R^1$ and $R^2$ are $CH_3$.

7. The compound of claim 6 wherein $C_1$ and $C_3$ have the R configuration.

8. The compound of claim 6 wherein X=I.

9. A compound of the formula (I):

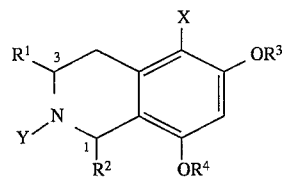

wherein X is Br, Cl or I, Y is H, $(C_1-C_4)$alkyl, benzyl, or CHO, each of $R^1$ and $R^2$ is H or $CH_3$, $R^3$ is H and $R^4$ is a protecting group selected from the group consisting of $(C_1-C_4)$alkyl, benzyl, $(C_2-C_5)$acyl and an acid-labile hydroxy protecting group.

10. The compound of claim 9 wherein $R^4$ is an acid-labile hydroxy protecting group.

11. The compound of claim 10 wherein the acid labile protecting group is $(C_1-C_4)$alkoxy$(C_1-C_4)$alkyl, tetrahydropyranyl, or $(R^8)_3Si$, wherein each $R^8$ is $(C_1-C_4)$alkyl.

12. The compound of claim 9 wherein $R^1$ and $R^2$ are $CH_3$.

13. The compound of claim 12 wherein $C_1$ and $C_3$ have the R configuration.

14. The compound of claim 12 wherein X=I.

15. A compound of the formula (I):

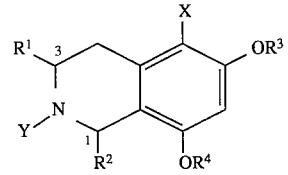

wherein X is Br, Cl or I, Y is H, $(C_1-C_4)$alkyl, benzyl, or CHO, each of $R^1$ and $R^2$ is H or $CH_3$, $R^3$ is a protecting group selected from the group consisting of $(C_1-C_4)$alkyl, benzyl, $(C_2-C)_5$acyl and an acid-labile hydroxy protecting group; and $R^4$ is H.

16. The compound of claim 15 wherein $R^3$ is an acid-labile hydroxy protecting group.

17. The compound of claim 16 wherein the acid labile protecting group is $(C_1-C_4)$alkoxy$(C_1-C_4)$alkyl, tetrahydropyranyl, or $(R^8)_3Si$, wherein each $R^8$ is $(C_1-C_4)$alkyl.

18. The compound of claim 15 wherein $R^1$ and $R^2$ are $CH_3$.

19. The compound of claim 18 wherein $C_1$ and $C_3$ have the R configuration.

20. The compound of claim 18 wherein X=I.

* * * * *